(12) United States Patent
Chen et al.

(10) Patent No.: US 7,223,548 B2
(45) Date of Patent: May 29, 2007

(54) METHOD OF SCREENING A CHEMICAL FOR BINDING TO A PROLINE-RICH NUCLEAR RECEPTOR CO-REGULATORY PROTEIN/NUCLEAR RECEPTOR COMPLEX

(75) Inventors: Shiuan Chen, Arcadia, CA (US); Dujin Zhou, Duarte, CA (US)

(73) Assignee: City of Hope, Duarte, CA (US)

( * ) Notice: Subject to any disclaimer, the term of this patent is extended or adjusted under 35 U.S.C. 154(b) by 89 days.

(21) Appl. No.: 11/035,096

(22) Filed: Jan. 14, 2005

(65) Prior Publication Data

US 2005/0202408 A1    Sep. 15, 2005

Related U.S. Application Data

(62) Division of application No. 09/552,705, filed on Apr. 19, 2000, now Pat. No. 6,972,178.

(60) Provisional application No. 60/129,873, filed on Apr. 19, 1999.

(51) Int. Cl.
| | |
|---|---|
| G01N 33/53 | (2006.01) |
| C12Q 1/68 | (2006.01) |
| C07K 1/00 | (2006.01) |
| A61K 38/24 | (2006.01) |
| C07H 21/02 | (2006.01) |

(52) U.S. Cl. .................... 435/7.1; 435/6; 530/350; 530/399; 536/23.1

(58) Field of Classification Search .............. 435/6, 435/7.1; 530/350, 399; 536/23.1
See application file for complete search history.

(56) References Cited

OTHER PUBLICATIONS

Zhou et al. Gene. Nov. 21, 2005;361:89-100. Epub Sep. 21, 2005.*
Agarwal, V.R. et al. "USe of Alternative Promoters to Express the Aromatase Cytochrome P450 (CYP19) Gene in Breast Adipose Tissues of Cancer-Free and Breast Cancer Patients", *J. Clin. Endocrinol. Metab.*, 1996; 81:3843-3849.
Bingle, C.D. "Generation of a Rat Bronchiolar Epithelial Cell cDNA Library: Isolation of a Proline Rich Protein Highly Enriched in Bronchiolar Epithelial Cells", *Biochemical and Biophysical Research Communications*, 1996; 225:877-882.
Boulikas, T. "Nuclear Localization Signals (NLS)", *Critical Reviews in Eukaryotic Gene Expression*, 1993; 3(3):193-227.
Cavaillès, V. et al. "Interaction of proteins with transcriptionally active estrogen receptors", *Proc. Natl. Acad. Sci. USA*, Oct. 1994; 91:10009-10013.
Cavaillès, V. et al. "Nuclear factor RIP 140 modulates transcriptional activation by the estrogen receptor", *The EMBO Journal*, 1995; 14(15):3741-3751.
Chakravarti, D. et al. "Role of CBP/P300 in nuclear receptor signalling", *Nature*, Sep. 5, 1996; 383:99-103.
Chen, J. et al. "Cloning a cDNA from human NK/T cells which codes for a protein with high proline content", *Biochimica et Biophysica Acta*, 1995; 1264:19-22.

Ding, X.F. et al. "Nuclear Receptor-Binding Sites of Coactivators Glucocorticoid Receptor Interacting Protein 1 (Grip1) and Steroid Receptor Coactivator 1 (SRC-1): Multiple Motifs with Different Binding Specificities", *Molecular Endocrinology*, 1998; 12:302-313.
Feng, S. et al. "Two Binding Orientations for Peptides to the Src SH3 Domain: Development of a General Model for SH3-Ligand Interactions", *Science*, Nov. 18, 1994; 226:1241-1247.
Glass, C.K. et al. "Nuclear receptor coativators", *Current Opinion in Cell Biology*, 1997; 9:222-232.
Halachmi, S. et al. "Estrogen Receptor-Associated Proteins: Possible Mediators of Hormone-Induced Transcription" *Science*, Jun. 3, 1994; 264:1455-1458.
Hanstein, B. et al. "p300 is a component of an estrogen receptor coactivator complex", *Proc. Natl. Acad. Sci. USA*, Oct. 1996; 93:11540-11545.
Harada, N. "Aberrant Expression of Aromatase in Breast Cancer Tissues", *J. Steroid Biochem. Molec. Biol.*, 1997; 61(3-6):175-184.
Heery, D.M. et al. "A signature motif in transcriptional co-activators mediates binding to nuclear receptors", *Nature*, Jun. 12, 1997; 387-733-736.
Hong, H. et al. "GRIP1, a novel mouse protein that serves as a transcriptional coactivator in yeast for the hormone binding domains of steroid receptors", *Proc. Natl. Acad. Sci. USA*, May 1996; 93:4948-4952.
Horwitz, K.B. et al. "Nuclear Receptor Coactivators and Corepressors", *Molecular Endocrinology*, 1996; 10:1167-1177.
Kamei, Y. et al. "A CBP Integrator Complex Mediates Transcriptional Activation and AP-1 Inhibition by Nuclear Receptors", *Cell*, May 3, 1996; 85:403-414.
Le Douarin, B. et al. "The N-terminal part of TIF1, a putative mediator of the ligand-dependent activation function (AF-2) of nuclear receptors, is fused to B-raf in teh oncogenic protein T18", *The EMBO Journal*, 1995; 14(9):2020-2033.
Lee, J.W. et al. "Interaction of thyroid-hormone receptor with a conserved trasncriptional mediator", *Nature*, Mar. 2, 1995; 374:91-94.

(Continued)

*Primary Examiner*—Teckchand Saidha
*Assistant Examiner*—Christian L. Fronda
(74) *Attorney, Agent, or Firm*—Rothwell, Figg, Ernst & Manbeck pc

(57) ABSTRACT

The invention relates to assays for screening for chemicals which affect the binding between proteins comprising an SH3 binding motif (such as Proline-rich Nuclear Receptor Co-regulatory protein (PNRC)) and nuclear receptor proteins. Compounds which affect the binding of PNRC to nuclear receptors can affect the expression of genes whose expression is under the control of nuclear receptors to which PNRC binds. PNRC interacts with the orphan receptors SF1 and ERRα1 in a ligand-independent manner and interacts with the ligand-binding domains of nuclear receptors such as ER, AR, PR, TR, BAR, and RXR in a ligand-dependent manner. A 23-amino acid region in the carboxy-terminal proline-rich region which contains an SH3-binding motif is sufficient for the interaction with nuclear receptors.

10 Claims, 12 Drawing Sheets

OTHER PUBLICATIONS

Onate, S.A. et al. "Sequence and Characterization of a Coactivator for the Steroid Hormone Receptor Superfamily", *Science*, Nov. 24, 1995; 270:1354-1357.

Pawson, T. "Protein modules and signalling networks", *Nature*, Feb. 16, 1995; 373:573-580.

Shibata, H. et al. "Role of Co-activators and Co-repressors in the Mechanism of Steroid/Thyroid Receptor Action", *Recent Progress in Hormone Research*, 1997; 52:141-165.

Suzuki, M. "SPXX, a Frequent Sequence Motif in Gene Regulatory Proteins", *J. Mol. Biol.*, 1989; 207:61-84.

Treuter, E. et al. "A Regulatory Role for RIP140 in Nuclear Receptor Activation", *Molecular Endocrinology*, 1998; 12:864-881.

Voegel, J.J. et al. "TIF2, a 160 kDa transcriptional mediator for the ligand-dependent activation function AF-2 of nuclear receptors", *The EMBO Journal*, 1996; 15(14):3667-3675.

vom Baur, E. et al. "Differential ligand-dependent interactions between the AF-2 activating domain of nuclear receptors and the putative transcriptional intermediary factors mSUG1 and TIF1", *The EMBO Jouranl*, 1996; 15(1):110-124.

Wang, J. et al. "Identification of a Promoter and a Silencer at the 3'-End of the First Intron of the Human Aromatase Gene", *Molecular Endocrinology*, 1992; 6:1479-1488.

Williamson, M.P. "The structure and function of a proline-rich regions in proteins", *Biochem. J.*, 1994; 297:249-260.

Yang, C. et al. "Modulation of Aromatase Expression in the Breast Tissue by ERRα-1 Orphan Receptor", *Cancer Research*; Dec. 15, 1998; 58:5695-5700.

Zhou, C. et al. "Aromatase Gene Expression and its Exon I Usage in Human Breast Tumors. Detection of Aromatase Messenger RNA by Reverse Transcription-polymerase Chain Reaction", *J. Steroid Biochem. Mol. Biol.*, 1996; 59(2):163-171.

Zhou, D. et al. "Characterization of a Silencer Element in the Human Aromatase Gene", *Archives of Biochemistry and Biophysics*, May 15, 1998; 353(2):213-220.

Zhou, D. et al. "Identification and Characterization of a cAMP-Responsive Element in the Region Upstream from Promoter 1.3 of the Human Aromatase Gene", *Archives of Biochemistry and Biophysics*, Nov. 15, 1999; 371(2):179-190.

Zhou, D. et al. "Identification of a Promoter That Controls Aromatase Expression in Human Breast Cancer And Adipose Stromal Cells", *The Journal of Biological Chemistry*, Jun. 21, 1996; 271(25):15194-15202.

Jordan, V.C. "Targeted Antiestrogens to Prevent Breast Cancer," *Trends Endocrinol. Metab*, 10(8):312-317, Oct. 1999.

Bentrem, D.J. et al., "Targeted Antiestrogens for the Prevention of Breast Cancer," *Oncol. Res.*, 11(9):401-107, 1999.

Levenson, A.S., "Selective Oestrogen Receptor Modulation: Molecular Pharmacology for the Millennium," *Eur. J. Cancer*, 35(14):1974-1985, Dec. 1999.

* cited by examiner

| E2- ESTRADIOL, 100 nM; | C-DEOXYCORTICOSTERONE, 10 µM; | P-PROGESTERONE, 500 nM; |
|---|---|---|
| T-DIHYDROTESTERONE, 100 nM; | T3-10 µM; | RA-ALL-TRANS-RETINOIC ACID, 10 µM; |
| 9c-RA-9-CIS-RETINOIC ACID, 10 µM; | | |

| | GROWTH ON | |
|---|---|---|
| cDNA EXPRESSION VECTORS | SD/-Leu/-Trp | SD/-Leu/-Trp/-His+3-AT |
| Gal4DB +Gal4AD | + | - |
| Gal4DB-SF1+Gal4AD | + | - |
| Gal4DB-SF1+AD-PNRC | + | + |
| hLCDB + AD-PNRC | + | - |
| Gal4DB-ERRα1+ Gal4 AD | + | - |
| Gal4DB-ERRα1 + AD-PNRC | + | + |
| Gal4DB-ER$_{HBD}$ + Gal4 AD | + | - |
| Gal4DB-ER$_{HBD}$ + AD-PNRC (E$_2$-) | + | - |
| Gal4DB-ER$_{HBD}$ + AD-PNRC (E$_2$*+) | + | + |
| Gal4DB-GR$_{HBD}$ + Gal4AD | + | - |
| Gal4DB-GR$_{HBD}$ + AD-PNRC (C-) | + | - |
| Gal4DB-GR$_{HBD}$ + AD-PNRC (C*+) | + | + |
| Gal4DB-PR$_{HBD}$ + Gal4AD | + | - |
| Gal4DB-PR$_{HBD}$ + AD-PNRC (P-) | + | - |
| Gal4DB-PR$_{HBD}$ + AD-PNRC (P*+) | + | + |
| Gal4DB-AR$_{HBD}$ + Gal4AD | + | - |
| Gal4DB-AR$_{HBD}$ + AD-PNRC (T-) | + | - |
| Gal4DB-AR$_{HBD}$ + AD-PNRC (T*+) | + | + |
| Gal4DB-TR$_{HBD}$ + Gal4AD | + | - |
| Gal4DB-TR$_{HBD}$ + AD-PNRC (T$_3$-) | + | - |
| Gal4DB-TR$_{HBD}$ + AD-PNRC (T$_3$*+) | + | + |
| Gal4DB-RAR$_{HBD}$ + Gal4AD | + | - |
| Gal4DB-RAR$_{HBD}$ + AD-PNRC (RA-) | + | - |
| Gal4DB-RAR$_{HBD}$ + AD-PNRC (RA*+) | + | + |
| Gal4DB-RXR$_{HBD}$ + Gal4AD | + | - |
| Gal4DB-RXR$_{HBD}$ + AD-PNRC (9c-RA -) | + | - |
| Gal4DB-RXR$_{HBD}$ + AD-PNRC (9c-RA *+) | + | + |

FIG. 1A

SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Sense -continued primer.

<400> SEQUENCE: 1
gccgaattcg gggagggcag gggtgaagtg                                      30

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:Antisense
      primer.

<400> SEQUENCE: 2
ggcgtcgacg gatcctcaga ctgtggcagg gaaaccctc                            39

<210> SEQ ID NO 3
<211> LENGTH: 12
<212> TYPE: DNA
<213> ORGANISM: Homo sapiens

<400> SEQUENCE: 3
ccaaggtcag aa                                                         12

<210> SEQ ID NO 4
<211> LENGTH: 5
<212> TYPE: PRT
<213> ORGANISM: Homo sapiens

<400> SEQUENCE: 4

Leu Lys Thr Leu Leu
 1               5

<210> SEQ ID NO 5
<211> LENGTH: 7
<212> TYPE: PRT
<213> ORGANISM: Homo sapiens

<400> SEQUENCE: 5

Ser Asp Pro Pro Ser Pro Ser
 1               5

<210> SEQ ID NO 6
<211> LENGTH: 7
<212> TYPE: PRT
<213> ORGANISM: Homo sapiens
<220> FEATURE:
<221> NAME/KEY: MUTAGEN
<222> LOCATION: (3)
<223> OTHER INFORMATION: This residue has been changed from a proline.
<220> FEATURE:
<221> NAME/KEY: MUTAGEN
<222> LOCATION: (6)
<223> OTHER INFORMATION: This residue has been changed from a proline.

<400> SEQUENCE: 6

Ser Asp Ala Pro Ser Ala Ser
 1               5

<210> SEQ ID NO 7
<211> LENGTH: 2061
<212> TYPE: DNA
<213> ORGANISM: Homo sapiens
<220> FEATURE:
<221> NAME/KEY: CDS
<222> LOCATION: (114)..(1094)

<400> SEQUENCE: 7

```
tgttccgcga tcttctcagg ctctcctagc agcatccatc gccgccaccc tatcttcact      60
ggcttcacct tctccttctc tcttcgttgc tgagcgacaa gcttcctagc gct atg       116
                                                             Met
                                                               1 act gtc gtc tcc gtc ccg cag cgg gag ccg ctc gtc ctg ggt ggc cgc      164
Thr Val Val Ser Val Pro Gln Arg Glu Pro Leu Val Leu Gly Gly Arg
         5                  10                  15 ctt gcg ccg ctt ggc ttt tcc tcc cga ggt tac ttt ggg gcc ctc ccg      212
Leu Ala Pro Leu Gly Phe Ser Ser Arg Gly Tyr Phe Gly Ala Leu Pro
     20                  25                  30 atg gtg acc acg gct ccg cct cct tta ccc cgg atc ccg gac ccc cgg      260
Met Val Thr Thr Ala Pro Pro Pro Leu Pro Arg Ile Pro Asp Pro Arg
 35                  40                  45 gca ctg ccc ccg acc ctc ttc ctc cct cat ttc cta ggg gga gat ggc      308
Ala Leu Pro Pro Thr Leu Phe Leu Pro His Phe Leu Gly Gly Asp Gly
 50                  55                  60                  65 ccg tgt ctg acc ccc cag cct cgc gct cca gca gct ctg ccc aac cgc      356
Pro Cys Leu Thr Pro Gln Pro Arg Ala Pro Ala Ala Leu Pro Asn Arg
             70                  75                  80 agc ctc gcc gtg gcg gga ggc act cct cgg gca gcg ccg aag aag cgg      404
Ser Leu Ala Val Ala Gly Gly Thr Pro Arg Ala Ala Pro Lys Lys Arg
         85                  90                  95 cga aag aag aag gtg cgg gcc agc ccc gca ggg cag ctg ccc agc cgc      452
Arg Lys Lys Lys Val Arg Ala Ser Pro Ala Gly Gln Leu Pro Ser Arg
     100                 105                 110 ttc cac cag tac cag cag cac cgg ccg agt ctg gag ggc ggc cgg agc      500
Phe His Gln Tyr Gln Gln His Arg Pro Ser Leu Glu Gly Gly Arg Ser
 115                 120                 125 ccc gcg acc ggc ccg agc gga gcg cag gag gtc ccg ggc ccg gcc gcc      548
Pro Ala Thr Gly Pro Ser Gly Ala Gln Glu Val Pro Gly Pro Ala Ala
130                 135                 140                 145 gcc ttg gcc ccg agt cct gca gcc gca gcc ggc acg gag gga gcc agc      596
Ala Leu Ala Pro Ser Pro Ala Ala Ala Ala Gly Thr Glu Gly Ala Ser
             150                 155                 160 ccc gac ctt gcc ccg ctg cgg ccc gcg gct ccc ggc caa acc ccc ctc      644
Pro Asp Leu Ala Pro Leu Arg Pro Ala Ala Pro Gly Gln Thr Pro Leu
         165                 170                 175 agg aaa gag gtt tta aaa tca aag atg gga aaa tcg gag aaa att gcc      692
Arg Lys Glu Val Leu Lys Ser Lys Met Gly Lys Ser Glu Lys Ile Ala
     180                 185                 190 ctt ccc cat ggc cag ctt gtt cat ggt ata cac ttg tat gag caa cca      740
Leu Pro His Gly Gln Leu Val His Gly Ile His Leu Tyr Glu Gln Pro
 195                 200                 205 aag ata aac aga cag aaa agc aaa tat aac ttg cca cta acc aag atc      788
Lys Ile Asn Arg Gln Lys Ser Lys Tyr Asn Leu Pro Leu Thr Lys Ile
210                 215                 220                 225 acc tct gca aaa aga aat gaa aac aac ttt tgg cag gat tct gtt tca      836
Thr Ser Ala Lys Arg Asn Glu Asn Asn Phe Trp Gln Asp Ser Val Ser
             230                 235                 240 tct gac aga att cag aag cag gaa aaa aag cct ttt aaa aat acc gag      884
Ser Asp Arg Ile Gln Lys Gln Glu Lys Lys Pro Phe Lys Asn Thr Glu
         245                 250                 255 aac att aaa aat tcg cat ttg aag aaa tca gca ttt cta act gaa gtg      932
Asn Ile Lys Asn Ser His Leu Lys Lys Ser Ala Phe Leu Thr Glu Val
     260                 265                 270 agc caa aag gaa aat tat gct ggg gca aag ttt agt gat cca cct tct      980
Ser Gln Lys Glu Asn Tyr Ala Gly Ala Lys Phe Ser Asp Pro Pro Ser
 275                 280                 285
```

```
cct agt gtt ctt cca aag cct cct agt cac tgg atg gga agc act gtt    1028
Pro Ser Val Leu Pro Lys Pro Pro Ser His Trp Met Gly Ser Thr Val
290                 295                 300                 305 gaa aat tcc aac caa aac agg gag ctg atg gca gta cac tta aaa acc    1076
Glu Asn Ser Asn Gln Asn Arg Glu Leu Met Ala Val His Leu Lys Thr
                310                 315                 320 ctc ctc aaa gtt caa act tagatttcag atttcagtat gtgtgtaaaa            1124
Leu Leu Lys Val Gln Thr
            325 cataatttt cccatatccc tggactcttg agaaaattgg tacagaaatg gaaatttgcc    1184
ttgttgcaac atacaattgc aaaagatgag tttaaaaaat tacatacaaa cagcttgtat   1244
tatatttat attttgtaaa tactgtatac catgtattat gtgtatattg ttcatacttg    1304
agaggtatat tatagttttg ttatgaaagt atgtattttg ccctgcccac attgcaggtg   1364
ttttgtatat atacaatgga taaattttaa gtgtgtgcta aggcacatgg aagaccgatt   1424
ttatttgcac aagtactga gatttttttc aagaaacagc tgtcaaatct caaggtgaag    1484
atctaaatgt gaacagttta ctaatgcact actgaagttt aaatctgtgg cacaatcaat   1544
gtaagcatgg ggtttgtttc tctaaattga tttgtaatct gaaattactg aacaactcct   1604
attcccattt ttgctaaact caatttctgg ttttggtata tatccattcc agcttaatgc   1664
ctctaattt aatgccaaca aaattggttg taatcaaatt ttaaaataat aataatttgg    1724
cccccccttt taaaatagtc ttgactcttt gtgtgtgact gtttctcatg tttgaatgtg   1784
tgactaggag atgattttgt gtggttggat ttttttgact tctactttac tggctgagtg   1844
tgagccgcca tgcctggcca taatctacat tttcttacca ggagcagcat tgaggttttt   1904
gagcatagta cttgactact ctagaggctg agacgggagc atctcttgag cctgagaagt   1964
ggagattgca attgagctag gatcaggcca ctgcactcca gcctgggtaa cagacgctgt   2024
ctcaaaaaaa aggccaagag aaagtaaggg agacaga                           2061
```

<210> SEQ ID NO 8
<211> LENGTH: 327
<212> TYPE: PRT
<213> ORGANISM: Homo sapiens

<400> SEQUENCE: 8

```
Met Thr Val Val Ser Val Pro Gln Arg Glu Pro Leu Val Leu Gly Gly
1               5                   10                  15

Arg Leu Ala Pro Leu Gly Phe Ser Ser Arg Gly Tyr Phe Gly Ala Leu
            20                  25                  30

Pro Met Val Thr Thr Ala Pro Pro Leu Pro Arg Ile Pro Asp Pro
        35                  40                  45

Arg Ala Leu Pro Pro Thr Leu Phe Leu Pro His Phe Leu Gly Gly Asp
    50                  55                  60

Gly Pro Cys Leu Thr Pro Gln Pro Arg Ala Pro Ala Leu Pro Asn
65                  70                  75                  80

Arg Ser Leu Ala Val Ala Gly Gly Thr Pro Arg Ala Ala Pro Lys Lys
                85                  90                  95

Arg Arg Lys Lys Lys Val Arg Ala Ser Pro Ala Gly Gln Leu Pro Ser
            100                 105                 110

Arg Phe His Gln Tyr Gln Gln His Arg Pro Ser Leu Glu Gly Gly Arg
        115                 120                 125

Ser Pro Ala Thr Gly Pro Ser Gly Ala Gln Glu Val Pro Gly Pro Ala
    130                 135                 140
```

```
Ala Ala Leu Ala Pro Ser Pro Ala Ala Ala Gly Thr Glu Gly Ala
145                 150                 155                 160

Ser Pro Asp Leu Ala Pro Leu Arg Pro Ala Ala Pro Gly Gln Thr Pro
                165                 170                 175

Leu Arg Lys Glu Val Leu Lys Ser Lys Met Gly Lys Ser Glu Lys Ile
            180                 185                 190

Ala Leu Pro His Gly Gln Leu Val His Gly Ile His Leu Tyr Glu Gln
        195                 200                 205

Pro Lys Ile Asn Arg Gln Lys Ser Lys Tyr Asn Leu Pro Leu Thr Lys
    210                 215                 220

Ile Thr Ser Ala Lys Arg Asn Glu Asn Asn Phe Trp Gln Asp Ser Val
225                 230                 235                 240

Ser Ser Asp Arg Ile Gln Lys Gln Glu Lys Lys Pro Phe Lys Asn Thr
                245                 250                 255

Glu Asn Ile Lys Asn Ser His Leu Lys Lys Ser Ala Phe Leu Thr Glu
            260                 265                 270

Val Ser Gln Lys Glu Asn Tyr Ala Gly Ala Lys Phe Ser Asp Pro Pro
        275                 280                 285

Ser Pro Ser Val Leu Pro Lys Pro Pro Ser His Trp Met Gly Ser Thr
    290                 295                 300

Val Glu Asn Ser Asn Gln Asn Arg Glu Leu Met Ala Val His Leu Lys
305                 310                 315                 320

Thr Leu Leu Lys Val Gln Thr
                325

<210> SEQ ID NO 9
<211> LENGTH: 23
<212> TYPE: PRT
<213> ORGANISM: Homo sapiens

<400> SEQUENCE: 9

Asn Tyr Ala Gly Ala Lys Phe Ser Asp Pro Pro Ser Pro Ser Val Leu
  1               5                  10                  15

Pro Lys Pro Pro Ser His Trp
             20
```

METHOD OF SCREENING A CHEMICAL FOR BINDING TO A PROLINE-RICH NUCLEAR RECEPTOR CO-REGULATORY PROTEIN/NUCLEAR RECEPTOR COMPLEX

CROSS REFERENCE TO RELATED APPLICATIONS

This application is a divisional of prior U.S. application Ser. No. 09/552,705, filed Apr. 19, 2000 now U.S. Pat. No. 6,972,178, which claims the benefit of U.S. provisional application Ser. No. 60/129,873 filed 19 Apr. 1999. The specifications of both applications above are hereby incorporated herein by reference in their entirety.

This application was made with Government support under Grant Nos. CA44735 and ES08258, funded by the National Institutes of Health, Bethesda, Md. The federal government may have certain rights in this invention.

BACKGROUND OF THE INVENTION

Steroid hormones, including estrogens, play an essential role in metabolism, sexual differentiation, and reproductive function. Considerable attention, therefore, has been directed to defining the mechanisms that control their biosynthesis. We have been studying the mechanisms that regulate the expression of the human aromatase gene in breast cancer. Aromatase catalyzes the conversion of androgens to estrogens and plays a key role in the pathogenesis of hormone-dependent breast cancer. An understanding of the mechanisms that regulate expression of the human aromatase gene will allow one to develop assays to screen for drugs for treating or preventing breast cancer, e.g., by screening for drugs which positively or negatively modulate transcription of the aromatase gene. Research from our laboratory has identified a silencer element (Wang and Chen, 1992; Zhou and Chen, 1998) that is situated between two aromatase promoters, 1.3 (Zhou et al., 1996a) and II (Wang and Chen, 1992; Zhou and Chen, 1998), which are thought to be the major promoters controlling aromatase expression in the ovary and in breast cancer tissue (Zhou et al., 1996b; Harada, 1997; Agarwal et al., 1996). UV cross-linking experiments (Wang and Chen, 1992; Zhou and Chen, 1998) have found that at least four proteins bind to the silencer element. Two orphan nuclear receptors, SF1 (Steroidogenic factor 1) and ERRα1 (Estrogen related receptor α-1), were shown to bind to this regulatory region (Yang et al., 1998). Cell transfection experiments have revealed that both SF1 and ERRα1 function as positive regulatory factors when they bind to the silencer element (Yang et al., 1998).

Nuclear receptors are transcription factors that modulate transcription of various cellular genes, either positively or negatively, by interacting with specific hormone-responsive elements located in the target gene promoters and thereby control diverse aspects of cell growth, development, and homeostasis. The mechanisms by which the nuclear receptors can regulate the transcription from the target gene promoters are currently under intensive investigation. Recent data show that, in addition to contacting the basal transcriptional machinery directly, nuclear receptors enhance or inhibit transcription by recruiting an array of coactivator and corepressor proteins to the transcription complex. Recently, a number of these putative co-regulatory proteins for nuclear receptors have been identified, and have been shown to act either as coactivators or as corepressors (reviewed in Horwitz et al., 1996; Shibata et al., 1997; Glass et al., 1997). Among the members of a growing family of coactivators are CBP and members of the SRC-1 gene family including SRC-1/p160 (Onate et al., 1995; Halachmi et al., 1994; Kamei et al., 1996), TIF2/GRIP-1 (Voegel et al., 1996; Hong et al., 1996; Ding et al., 1998), and CBP/p300 (Chakravarti et al., 1996; Hanstein et al., 1996) which function as coactivators of nuclear receptors, and also RIP140 (Cavailles et al., 1994; Cavailles et al., 1995), TIF1 (Le Douarin et al., 1995) and TRIP1/SUG-1 (Lee et al., 1995; vom Baur et al., 1996), the functions of which are not clearly defined. Most of these cofactors of nuclear receptors have a molecular weight around 160 kDa, and share a common motif containing a core consensus sequence LXXLL (L, leucine; X, any amino acid), which is necessary and sufficient to mediate the binding of these proteins to liganded nuclear receptors. LXXLL is thus a defining feature of p160 coactivators (Heery et al., 1997).

Although these cofactors are of interest, additional co-activators and co-repressors are sought, especially those which interact with receptors via a novel binding motif.

The publications and other materials used herein to illuminate the background of the invention or provide additional details respecting the practice are incorporated by reference and for convenience are respectively grouped in the appended List of References.

SUMMARY OF THE INVENTION

A protein named proline-rich nuclear receptor co-regulatory protein (PNRC) (SEQ ID NOs:7 and 8 represent the gene and protein sequences of PNRC) has been found to be a novel type of nuclear receptor coactivator which binds to nuclear receptors including those which regulate the human aromatase gene which is involved in development of breast cancer. PNRC binds to nuclear receptors via a different motif than that of a number of known coactivators. As a result, drug screening assays utilizing PNRC will result in finding of useful drugs, such as for treating breast cancer, which would be missed by screens using a different class of nuclear receptor coactivator.

One aspect of the invention is a method of screening a chemical for its ability to enhance the binding of a co-regulatory protein to a nuclear receptor or to a nuclear receptor ligand binding domain. More particularly, this aspect of the invention is directed to screening a chemical by cotransfecting cells with i) a gene which expresses a co-regulatory protein comprising SDPPSPS (SEQ ID NO:5) and ii) a nucleic acid comprising a gene encoding a nuclear receptor or a nuclear receptor ligand binding domain to produce cotransfected cells which synthesize said co-regulatory protein and said nuclear receptor or said nuclear receptor ligand binding domain, and further wherein said cotransfected cells comprise a reporter gene the expression of which depends upon said co-regulatory protein binding to said nuclear receptor or to said nuclear receptor ligand binding domain, growing separate portions of the cotransfected cells in the presence and in the absence of said chemical, and determining the level of expression of the reporter gene in each portion of cotransfected cells to determine whether the chemical enhances binding of the co-regulatory protein to the nuclear receptor or to the nuclear receptor ligand binding domain.

A second aspect of the invention is a method of screening for a chemical for its ability to inhibit the binding of a co-regulatory protein to a nuclear receptor or to a nuclear receptor ligand binding domain. More particularly, this aspect of the invention is directed to screening a chemical by cotransfecting cells with i) a gene which expresses a co-regulatory protein comprising SDPPSPS (SEQ ID NO:5) and ii) a nucleic acid comprising a gene encoding a nuclear receptor or a nuclear receptor binding domain to produce cotransfected cells which synthesize said co-regulatory protein and said nuclear receptor or said nuclear receptor ligand binding domain, and further wherein said cotransfected cells comprise a reporter gene the expression of which depends upon said co-regulatory protein binding to said nuclear receptor or to said nuclear receptor ligand binding domain, growing separate portions of the cotransfected cells in the presence and in the absence of said chemical, and determining the level of expression of the reporter gene in each portion of cotransfected cells to determine whether the chemical inhibits binding of the co-regulatory protein to the nuclear receptor or to the nuclear receptor ligand binding domain.

A third aspect of the invention is a method of screening a chemical to determine if it has activity similar to a known chemical such as a hormone. More particularly, this aspect of the invention is directed to screening a chemical by cotransfecting cells with i) a gene which expresses a co-regulatory protein comprising SDPPSPS (SEQ ID NO:5) and ii) a nucleic acid comprising a gene encoding a nuclear receptor or said nuclear receptor ligand binding domain to produce cotransfected cells which synthesize said co-regulatory protein and said nuclear receptor or said nuclear receptor ligand binding domain, and further wherein said cotransfected cells comprise a reporter gene the expression of which depends upon said co-regulatory protein binding to said nuclear receptor or to said nuclear receptor ligand binding domain, and further wherein said co-regulatory protein binds to said nuclear receptor or to said nuclear receptor ligand binding domain in the presence of said known chemical, growing a first portion of said cotransfected cells in the presence of said test chemical, growing a second portion of said cotransfected cells in the absence of said chemical, and determining the level of expression of said reporter gene in each portion of cells to determine whether the test chemical results in reporter gene expression similar to the expression produced by the known chemical.

Another aspect of the invention is a method of determining a concentration of a ligand or a hormone in a tissue sample. More particularly, this aspect of the invention is directed to determining a concentration of a ligand or a hormone in a tissue sample, wherein said method comprises cotransfecting cells with i) a gene which expresses a co-regulatory protein comprising SDPPSPS (SEQ ID NO:5) and ii) a nucleic acid comprising a gene encoding a nuclear receptor or said nuclear receptor ligand binding domain to produce cotransfected cells which synthesize said co-regulatory protein and said nuclear receptor or said nuclear receptor ligand binding domain, and further wherein said cotransfected cells comprise a reporter gene the expression of which depends upon said co-regulatory protein binding to said nuclear receptor or to said nuclear receptor ligand binding domain, and further wherein said co-regulatory protein binds to said nuclear receptor or to said nuclear receptor ligand binding domain in the presence of said ligand or hormone, preparing an extract of said tissue sample, growing a first portion of said cotransfected cells in the presence of said tissue extract, growing second portions of said cotransfected cells in the presence of known concentrations of said ligand or hormone, and determining the level of expression of said reporter gene in each portion of cells, wherein the concentration of said ligand or said hormone in said tissue extract can be determined by comparison of the expression level of said reporter gene in said first portion with the expression levels of said reporter gene in said second portions.

Another aspect of the invention is a method of using a two-hybrid screening assay to screen a library for a gene encoding a protein which binds to a specific chemical. More particularly, this aspect of the invention is directed to a method of screening for a protein which interacts with a chemical, wherein said method comprises cotransfecting cells with i) a gene which expresses a co-regulatory protein comprising SDPPSPS (SEQ ID NO:5) and ii) a library of nucleic acids to produce a library of cotransfected cells which synthesize said co-regulatory protein and said library of nucleic acids, and further wherein said cotransfected cells comprise a reporter gene the expression of which depends upon said co-regulatory protein binding to a nuclear receptor or to a nuclear receptor ligand binding domain, and further wherein said co-regulatory protein binds to said nuclear receptor or to said nuclear receptor ligand binding domain in the presence of said chemical, growing colonies of said cotransfected cells in the presence of said chemical, and determining the level of expression of said reporter gene in individual colonies of cells, wherein colonies of cells which express said reporter gene comprise a gene from said library encoding a protein which interacts with said chemical.

BRIEF DESCRIPTION OF THE FIGURES

FIGS. 1A-C show the interaction between PNRC and nuclear receptors in yeast. Yeast strains Y187, expressing the Gal4DBD fusion to the nuclear receptors, and CG1945, expressing Gal4AD alone or Gal4Ad-PNRC fusion protein, were mated by coculture, and selected for the presence of both two-hybrid plasmids. The expression of interacting hybrid proteins in yeast diploids was analyzed for induction of HIS3 expression (FIG. 1A) and LacZ expression (FIGS. 1B and 1C) in the presence of the indicated amount of ligands as described in Example 1. Gal4AD was included as a control to monitor the background transcriptional activity. Relative β-galactosidase activities in liquid cultures were expressed in $OD_{420}$ as mean±S.D. of three independent assays. Hormones used in FIGS. 1B and 1C are the same as for FIG. 1A.

FIG. 4A shows the effect of PNRC on SF1-stimulated transcription of promoter 1.3 of the human aromatase gene. SK-BR-3 cells were transfected with 2.5 µg of p1.3aroCAT-(SF1site)$_3$ reporter along with 5 ng of a pSG5-SF1 expression plasmid and an amount of pSG5-PNRC expression plasmid as indicated below the figure. Appropriate amounts of empty vector, pSG5, were included to maintain the overall same amount of total DNA in all transfections. The CAT activities in transfected cells were measured as described in Example 5, and expressed as mean±S.D. of at least triplicate experiments. FIG. 4B shows the effect of PNRC on ERRα1-stimulated transcription of promoter 1.3 of the human aromatase gene. SK-BR-3 cells were transfected with p1.3CAT-(SF1site)$_3$ reporter along with either pSG5-ERRα1 expression plasmid, pSG5-PNRC or both as indicated below the figure. All other features are as described in FIG. 4A. FIG. 4C shows the effect of PNRC on SF1-mediated transcription of thymidine kinase promoter. SK-BR-3 cells were transfected with ptkCAT-(SF1 site)$_3$ reporter along with either pSG5-SF1 expression plasmid, pSG5-PNRC expression plasmid, or both as indicated below the figure. All other features are the same as in FIG. 4A. FIG. 4D shows the effect of PNRC on ERRα1-mediated transcription of thymidine kinase promoter. SK-BR-3 cells were transfected with ptkCAT-(SF1site)$_3$ reporter along with either pSG5-ERRα1 expression plasmid, pSG5-PNRC expression plasmid, or both as indicated below the figure. All other conditions are the same as in FIG. 4A.

DETAILED DESCRIPTION OF THE INVENTION

Figure 1B:
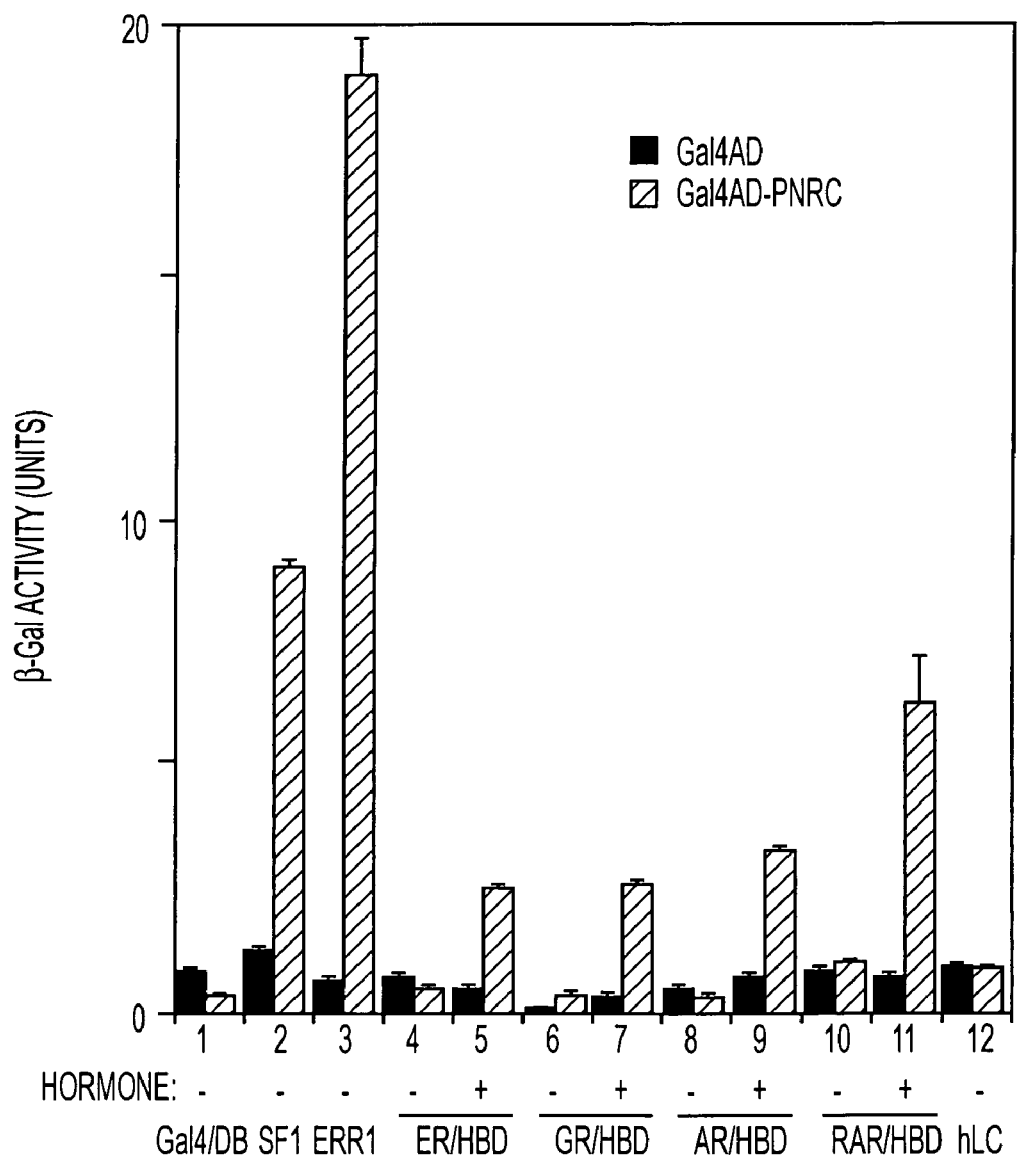

In order to better understand the regulatory mechanism of nuclear receptors and hormone binding domains such as SF1, ERRα1, ER, AR, PR, TR, RAR and RXR on aromatase expression, a search was made for co-regulatory proteins interacting with these proteins using bovine SF1 as the bait in a yeast two-hybrid screening of a human mammary gland cDNA expression library. This search resulted in the isolation of several clones, one of which encodes a protein named proline-rich nuclear receptor co-regulatory protein (PNRC).

PNRC was previously named B4-2 and was first isolated by differential screening of a human natural killer (NK) cell line library (Chen et al., 1995), and then its rat homologue was isolated from a rat bronchiolar epithelial cell cDNA library (Bingle, 1996). PNRC encodes a deduced 327 aa protein (SEQ ID NO:8) with a calculated molecular mass of 35 kDa. This protein exhibits interesting structural features. It is very rich in proline, from 13.4% in human PNRC to 14.4% in the rat homologue. The exact function of proline rich regions in proteins remains unclear. However, in many proteins it appears that they mediate functionally important binding reactions (Williamson, 1994). PNRC also contains several SPXX or TPXX sequence motifs; proteins rich in these two motifs are a sign of gene regulatory proteins (Suzuki, 1989). There is a potential nuclear localization sequence located at position 94-101 of PNRC. This sequence is thought to be necessary for nuclear proteins to translocate into the nucleus (Boulikas, 1993). Based on these structural features, PNRC has been postulated to be involved in gene regulation (Chen et al., 1995). In the present study, PNRC was isolated through its interaction with the orphan receptor SF1. The results generated from yeast and mammalian two-hybrid assays, in vitro binding assays, and functional analysis have provided several lines of evidence supporting that PNRC is a general co-regulatory protein for the nuclear receptor superfamily.

Unlike most of the coactivators, the interactions of which with the nuclear receptors depend on an LXXLL motif, the interaction between PNRC and the nuclear receptors is dependent on an S-D-P-P-S-P-S (SEQ ID NO:5) core ligand motif for SH3 in a stretch of proline-rich sequence at its carboxy-terminus, aa 278-300 (shown separately as SEQ ID NO:9). This domain was not found in other nuclear receptor coactivators including SRC1, GRIP1, RIP140, TIFI, TIFII, ARA70, and CBP/p300 in a BLAST sequence homology search, suggesting that different parts of the nuclear receptors participate in the formation of the binding interface with PNRC as compared with the parts that participate with the p160 coactivator family the binding site of which is an NR box. This exact 23 amino acid sequence is also found to be present in another protein isolated from the same yeast two-hybrid screening. Taken together, these proteins including PNRC apparently belong to a new family of nuclear receptor co-regulatory proteins. Considering the core ligand motif for SH3 in PNRC, in addition to its function as a nuclear receptor coactivator, PNRC also may play a role in signal transduction since most of the proteins possessing SH3 domains are involved in signal transduction (Pawson, 1995). Furthermore, since PNRC interacts with nuclear receptor LBDs in a ligand-dependent manner, a PNRC/nuclear receptor LBD coexpression system will be useful for screening ligands or drugs that bind to the nuclear receptors. Similarly, such a system is useful for screening for compounds which inhibit binding of ligands to the nuclear receptors. A two-hybrid system including PNRC can be used to screen for compounds which have activity like a known ligand, taking advantage of the fact that the co-regulatory protein binds to the nuclear receptor in a ligand dependent manner. Assays with PNRC can also be developed to measure ligand or hormone concentration in a tissue. Also, PNRC can be used as the bait in conjunction with a ligand in assays to find other proteins which interact with the ligand. In addition, since PNRC interacts with nuclear receptors in a different fashion from other known co-regulatory proteins (that use the NR box), the ligands or proteins identified using the PNRC/nuclear receptor LBD co-expression system may not be the same as those identified by the traditional approaches. PNRC interacts strongly with TR, PR and RXR and so the identified ligands for these nuclear receptors may be important modulators of the action of these nuclear receptors in cells. The co-expression system can be developed using, e.g., yeast or mammalian cell culture.

The nuclear receptor binds to its target gene, e.g., aromatase, in conjunction with the co-regulatory protein and a ligand. The ligand is required for the co-regulatory protein to bind to the nuclear receptor. When the ligand, co-regulatory protein and nuclear receptor are bound to the target gene, the target gene activity is affected. This can be a positive regulation or a negative regulation depending upon the specific gene being regulated. Chemicals which act as ligands to promote the binding of the co-regulatory protein to the nuclear receptor, thereby increasing binding of the nuclear receptor to the target gene, can be discovered by screening chemicals using a two-hybrid assay. In the two hybrid assay, cells are cotransfected with two nucleic acids, one of which encodes the co-regulatory protein and the second of which encodes the nuclear receptor or minimally the nuclear receptor ligand binding domain. Additionally, the cotransfected cells are engineered to include a reporter gene, the expression of which is dependent upon the co-regulatory protein binding to the nuclear receptor or to the nuclear receptor ligand binding domain. When the cotransfected cells are grown in the absence of a ligand the expression of the reporter gene will be minimal. When the cotransfected cells are grown in the presence of a chemical which acts as a ligand to promote the binding of the co-regulatory protein to the nuclear receptor or to the nuclear receptor ligand binding domain, the expression of the reporter gene will be increased as compared to its expression level when the cells are grown in the absence of any effective ligand. Many different reporter genes have been reported in the literature and are known to those of skill in the art. For example, genes which cause the production of histidine have been used as reporter genes. The CAT gene is also widely used as a reporter gene.

These assays can be designed to screen for chemicals which act as known ligands. For example, PNRC interacts with hormone binding domain ER when estradiol is present. A two-hybrid system utilizing cells which express PNRC and ER will synthesize a reporter gene in the presence of estradiol but not in the absence of estradiol. Chemicals which can act as estradiol causing PNRC and ER to interact can be screened in a two-hybrid assay in which the cells express PNRC and ER but are grown in the absence of estradiol and in the presence of a test chemical. If the test chemical causes expression of the reporter gene then the test chemical will have estradiol-like activity. Similarly, assays for screening chemicals which will act as other ligands, e.g., deoxycorticosterone, dihydrotestosterone, progesterone, T3, all-trans-retinoic acid or 9-cis-retinoic acid, can be developed by preparing a two-hybrid system which expresses PNRC and a hormone binding domain appropriate for the hormone, e.g., GR, AR, PR, TR, RAR or RXR.

Similarly, this same two-hybrid assay system can be utilized to screen for chemicals which inhibit the binding of the co-regulatory protein to the nuclear receptor. This latter method of screening is preferably performed in the presence of a ligand which is known to promote the binding of the co-regulatory protein to the nuclear receptor, thereby resulting in a high expression of the reporter gene. In such an assay, chemicals which decrease the expression of the reporter gene are selected as those which inhibit the binding of the co-regulatory protein to the nuclear receptor.

Assays to measure ligand or hormone concentrations in tissue, e.g., in breast tissue, can be performed using PNRC in a two-hybrid assay. Knowledge of specific hormone levels is often important when treating disease, e.g., knowledge of estrogen levels is important when treating breast cancer. Because of the requirement for a ligand to allow the interaction between PNRC and a nuclear receptor, a two-hybrid assay system can be developed in which the cells are cotransfected to express PNRC and a specific receptor. In the absence of added ligand or hormone the cells will not express the reporter gene. Addition of a tissue extract, containing an unknown concentration of ligand or hormone, to the cells of the two-hybrid assay will result in the expression of the reporter gene if the ligand or hormone required for interaction of PNRC and the nuclear receptor is present in the tissue extract. The concentration of the ligand or hormone can be calculated from the amount of expression of the target gene by comparing the results to expression of the target gene using known concentrations of the ligand or hormone.

PNRC is also useful in performing assays to discover proteins or receptors which interact with ligands or hormones. As an example, tamoxifen is used to treat breast cancer but often resistance to the drug develops. This resistance may develop as a result of a protein being expressed which binds to the tamoxifen. To screen for such a protein, a two-hybrid system is designed in which PNRC is used as the bait. The assay is designed such that cells are cotransfected with PNRC and with a library of other genes. These are grown in the presence of tamoxifen. Cells are assayed for the expression of a reporter gene. A cell-type which expresses the reporter gene is cultured and assayed to determine the gene which it contained. This gene will encode a protein which interacts with PNRC and tamoxifen. Such an assay allows one to screen for proteins which interact with a ligand. This is different from the typical two-hybrid assay which is used to find two proteins which interact with each other rather than to find a protein and a ligand which interact with each other.

The present invention is further detailed in the following Examples, which are offered by way of illustration and are not intended to limit the invention in any manner. Standard techniques well known in the art or the techniques specifically described below are utilized.

EXAMPLE 1

Yeast Two-Hybrid Assays

The protein-protein interactions between the full-length PNRC or PNRC fragments and SF1, ERRα1, and several other nuclear receptors were analyzed by yeast two-hybrid assays. The yeast two-hybrid assay was used to test if PNRC also interacts with other members of the nuclear receptor superfamily. pGBT9-ERRα-1 yeast expression plasmid was prepared by inserting the PCR-amplified ERRα-1 coding region into pGBT9 through an EcoRI site. To construct the plasmid pGBT9-ER$_{274-595}$, the coding sequence from amino acids 274 to 595 (LBD) of ERα was amplified by PCR with the sense primer 5'-GCCGAATTCGGG-GAGGGCAGGGGTGAAGTG-3' (SEQ ID NO:1) and anti-sense primer 5'-GGCGTCGACGGATCCTCAGACTGTG-GCAGGG AAACCCTC-3' (SEQ ID NO:2) and cloned into the EcoRI/SalI site of the pGBT9 yeast expression plasmid. pSG5-GRIP1 and several yeast expression plasmids coding for fusion proteins of Gal4-DBD and HBDs of AR, GR, PR, TR, RAR, and RXR in pGBT9 vector were kindly provided by Dr. Michael R. Stallcup (University of Southern California, Los Angeles, Calif.) (Voegel et al., 1996; Hong et al., 1996; Ding et al., 1998). The yeast mating approach was used in yeast two-hybrid assays to study protein-protein interactions as described in Clontech's protocol. Briefly, pGBT9 (DNA-BD vector only), pGBT9/target plasmids for SF1, ERRα1, and other HBDs of nuclear receptors, and DNA-BD/control plasmids (as negative control) were introduced into the reporter strain Y187, and the AD vector alone or wild type PNRC and its deleted fragments-containing pACT2 derivatives were used to transform yeast strain CG1945. The yeast mating was performed by picking one colony from each type and growing both colonies in liquid YPD medium with or without a proper ligand at the following concentrations: 100 nM of estradiol for ER; 10 μM of deoxycorticosterone for GR; 100 nM of dihydrotestosterone for AR; 500 nM of progesterone for PR; 10 μM of T3 for TR; 10 μM of all-trans-retinoic acid for RAR; and 10 μM of 9-cis-retinoic acid for RXR. The same amount of an aliquot of the mating culture was spread on both SD/-Leu/-Trp plates to select diploid strains bearing both plasmids and SD/-Leu/-Trp/-His/+3-AT plates to score the growth of the diploid cells that express the two interacting target proteins. The His3 positive colonies were further analyzed for β-galactosidase activity by liquid β-galactosidase activity measurement as essentially described in the protocol.

Figure 1C:
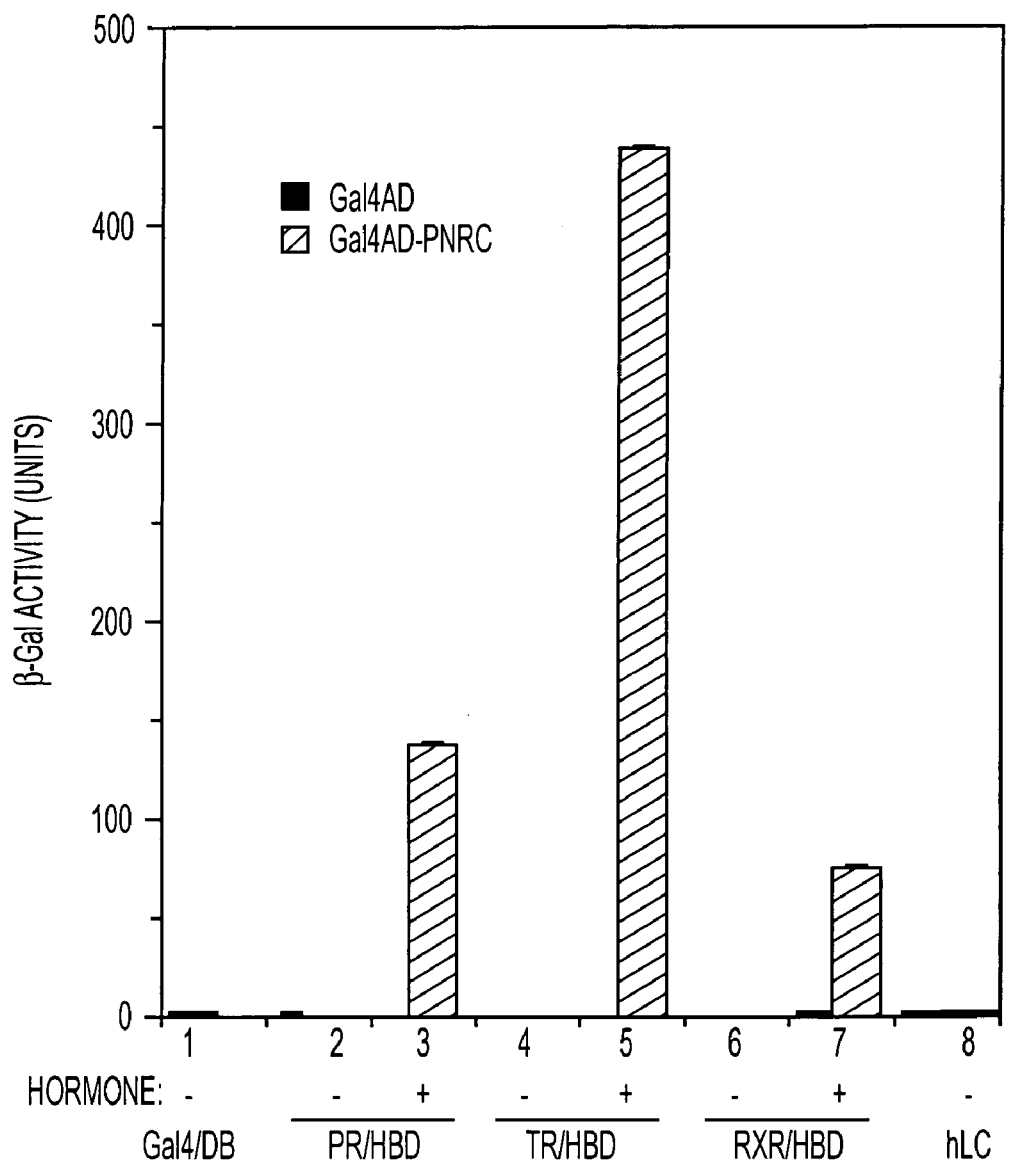

Yeast strains Y187 expressing the Gal4DB fusion to the nuclear receptors and CG1945 expressing Gal4AD alone or Gal4AD-PNRC fusion protein were mated by co-culturing, and selected for the presence of both two-hybrid plasmids. The expression of interacting hybrid proteins in yeast diploids was analyzed to determine if there was induction of HIS3 expression as shown in FIG. 1A and LacZ expression as shown in FIGS. 1B and 1C. Tests in yeast two-hybrid assays indicated that PNRC interacted with orphan receptors SF1 and ERRα1 in the absence of any added activator or ligand. As shown in FIGS. 1A-C, PNRC also interacted specifically with all seven nuclear receptor HBDs, including ER, AR, GR, TR, PR, RAR and RXR, and these interactions were completely ligand-dependent. The results also showed that PNRC interacted with these nuclear receptors with different preferences. PNRC interacts strongly with TR, PR, and RXR in the presence of cogent ligands (FIG. 1C), whereas only weak interactions were detected between PNRC and ER, GR, AR and RAR (FIG. 1B). However, no interactions occurred either between PNRC and an irrelevant protein such as human lamin C protein or between nuclear receptors and Gal4 activation domain alone. These results suggest that the interaction occurred only in the presence of PNRC and nuclear receptors in the forms of two-hybrid proteins and that PNRC is a broad nuclear receptor-interacting protein which preferentially associates with ligand-bound nuclear receptors.

EXAMPLE 2

Mammalian Two-Hybrid Assays

The Mammalian MatchMaker two-hybrid assay system (Clontech) was used to confirm the interaction between PNRC and SF1 that was identified in the yeast assays. Because the assays are performed in mammalian cells, proteins are more likely to be in their native conformations, and the results are therefore more likely to represent biologically significant interactions. SK-BR-3 breast cancer cells were cotransfected with three expression plasmids, including pM-SF1 for Gal4 DNA-DB/SF1 fusion protein, pVP16-PNRC for VP16AD-PNRC fusion protein, and a third vector, pG5CAT, to provide the Gal4 DNA-binding site, a promoter, and the CAT reporter gene.

A set of plasmids, named pM-SF1, pVP16-PNRC, pVP16-PNRC$_{270-327}$, and pVP16-PNRC$_{278-300}$, for mammalian two-hybrid assays were prepared as follows: SF1 cDNA fragment was excised from pGBT9-SF1 and inserted in frame into Gal4 DNA-binding domain vector pM (Clontech) through an EcoRI site. PCR was used to generate PNRC full length coding region as well as the above mentioned deleted fragments with BclI at both ends. The PCR products were digested with BclI and inserted in proper reading frame into a pVP16 activation domain vector (Clontech) at a BamHI site. Mammalian two-hybrid assays in SK-BR-3 cells were performed according to the procedures described in the Clontech protocol (PT3002-1).

Figure 2:
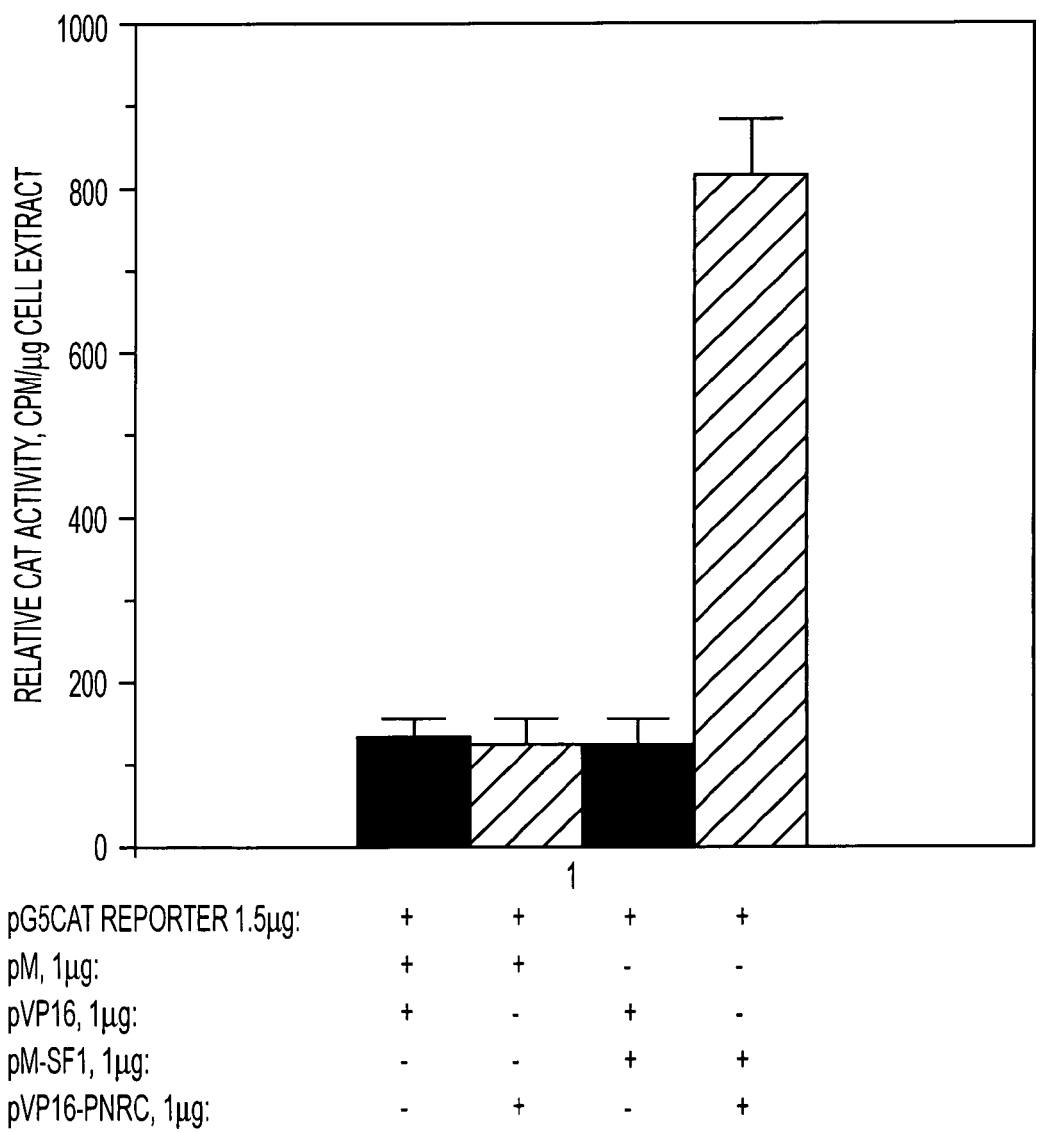
FIG. 2 shows the interaction of PNRC with SF1 in mammalian cells. SK-BR-3 cells were transiently cotransfected with 1.5 µg reporter plasmid, pG5CAT, and 1.0 µg each of expression plasmids for SF1 and wild type PNRC or for PNRC fragments. The relative CAT activities were expressed as mean±S.D. of three experiments.

As shown in FIG. 2, the CAT activities of the cells transfected with the above three plasmids are about 5-6 fold higher than that of the cells transfected with only CAT reporter plasmid. This interaction of PNRC is specific for SF1 since no interaction was observed either between PNRC and Gal4 DB or between SF1 and VP16 AD.

EXAMPLE 3

GST Pull-Down Assays

To further confirm the interaction between PNRC and SF1 which was detected in both the yeast and the mammalian two-hybrid assays, a GST pull-down binding assay was performed to study the direct binding between PNRC and SF1 in vitro. The PNRC cDNA fragments were generated by PCR and inserted into E. coli expression vector pGEX2TK (Pharmacia) through a BamHI site to express GST-PNRC wild type and deletion mutants fusion proteins. Wild type bovine SF1 cDNA in pSG5 vector was translated in vitro in the presence of [$^{35}$S]methionine using the TNT Coupled Reticulocyte Lysate System (Promega, Madison, Wis.). GST and deleted PNRC fusion proteins, GST-PNRC$_{270-327}$ and GST-PNRC$_{278-300}$, were prepared using the affinity matrix Glutathione Sepharose 4B (Pharmacia) according to the supplier's instructions. The washed beads containing about 10 μg GST fusion protein were incubated for 2 hour at 4° C. with 4 μl in vitro translated, [$^{35}$S]methionine-labeled SF1 in a total volume of 150 μl incubation buffer (50 mM Kpi, pH 7.4, 100 mM NaCl, 1 mM MgCl$_2$, 10% glycerol, 0.1% Tween 20, 1.5% BSA) (Treuter et al., 1998). Beads were collected and washed three times with incubation buffer without BSA. Washed beads were resuspended in 50 μl of 1×SDS sample buffer, boiled in water for 5 minutes, and pelleted briefly in a microfuge. 25 μl of the supernatant along with ⅒ of the input, [$^{35}$S]methionine-labeled SF1 were then subjected to 10% SDS-PAGE. To control the equal loading of GST fusion proteins, gel was stained with Coomassie blue before being visualized by autoradiography.

Figure 3A:
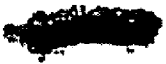
FIGS. 3A-B show the interaction of PNRC with SF1 in vitro. $^{35}$S-labeled, in vitro translated SF1 was incubated with Sepharose beads containing bound GST-PNRC$_{270-377}$, GST-PNRC$_{278-300}$, or GST protein. The beads were washed and bound protein was eluted and analyzed by SDS-PAGE. The gel was stained with Coomassie blue (FIG. 3B) before being visualized by autoradiography (FIG. 3A). An aliquot of the in vitro translated SF1 equivalent to 10% of sample employed for the binding reactions was also analyzed (input).
Figure 3B:

Our results from the yeast two-hybrid assays showed that a short 23-residue region in PNRC was sufficient for the interaction between PNRC and the nuclear receptors (explained in detail below). PNRC fragments, including PNRC$_{270-327}$ and PNRC$_{278-300}$, were expressed as fusion proteins with glutathione S-transferase (GST) in E. coli BL21, purified with glutathione Sepharose 4B beads, and tested for their ability to bind in vitro translated [$^{35}$S] methionine-labeled SF1 in pull-down assays. As shown in FIGS. 3A-B, both GST-PNRC$_{270-327}$ and GST-PNRC$_{278-300}$ were found to bind SF1 (FIGS. 3A-B, lanes 3 and 4). The results also showed that the binding of SF1 was specific to PNRC, because GST alone only retained very small amounts of labeled SF1 (FIG. 3A, lane 2) even when the bead-bound GST protein was in excess as shown by Coomassie blue staining in FIG. 3B.

EXAMPLE 4

Isolation of Clones Encoding Proteins which Interact with SF1

In order to better understand the regulatory mechanism of nuclear receptors and hormone binding domains such as SF1, ERRα1, ER AR, PR, TR, RAR and RXR on aromatase expression, a search was made for co-regulatory proteins interacting with these proteins using bovine SF1 as the bait in a yeast two-hybrid screening of a human mammary gland cDNA expression library. A Gal4-based yeast two-hybrid system was used to identify proteins encoded in a human mammary gland cDNA library that interact with the bovine SF1. The coding region for the wild type bovine SF1 was first subcloned into a yeast expression vector, pGBT9, and the resulting plasmid, pGBT9-SF1, was used to transform CG1945. The coding region of yeast expression plasmid for $DBDG_{Gal4}$-SF1 fusion protein, named pGBT9-SF1, was made by inserting PCR-amplified cDNA fragment coding for bovine SF1 into an EcoRI site of pGBT9 vector (Clontech). For the two-hybrid screening, yeast strain CG1945 containing pGBT9-SF1 plasmid was transformed with a human mammary gland MATCHMAKER cDNA expression library (Clontech) in the Gal4 activation domain vector (pACT2, Clontech). Transformants ($3.42 \times 10^6$) were first screened in the absence of ligand, since the ligand for SF1 is unknown, for HIS3 reporter gene expression and then further screened for β-galactosidase activity. A total of 90 colonies appeared on the histidine dropout plates, 12 of which stained strongly positive when tested for expression of β-galactosidase. Plasmids of the twelve His$^+$ and β-galactosidase positive transformants were isolated, and the nucleotide sequences of inserts were determined. The identity of the cDNAs was determined through a homology search against known sequences in GenBank. The database search revealed that 4 out of the 12 clones are identical to a portion of B4-2, a proline-rich protein, which was first cloned from a natural killer minus T cell subtractive library with unknown function (Chen et al., 1995). These clones are here designated as PNRC (Proline-rich Nuclear Receptor Co-regulatory protein). Another three clones are identical to a known nuclear receptor coactivator, RIP140 (Cavailles et al., 1994; Cavailles et al., 1995). In addition to PNRC and RIP140, we also isolated two clones encoding one unknown protein with high homology to PNRC as well as three clones encoding three other unknown proteins.

EXAMPLE 5

Effect of PNRC on Nuclear Receptor Transactivation

PNRC has been demonstrated to specifically interact with multiple members of the nuclear receptor family in vivo and in vitro. To examine the possible biological significance of this interaction, the entire PNRC coding region was inserted into a mammalian expression vector, pSG5, and this expression plasmid was used to transiently transfect SK-BR-3 cells along with a reporter plasmid, pUMS1.3CAT-(SF1site)$_3$, which contains three copies of extended steroid hormone half binding site from the human aromatase gene (5'-CCAAGGTCAGAA-3' (SEQ ID NO:3)), promoter 1.3 of the human aromatase gene, and the CAT reporter gene, along with a second expression plasmid for either SF1 (pSG5-SF1) or ERRα1 (pSG5-ERRα1) (Yang et al., 1998).

Plasmid for overexpression of PNRC in mammalian cells was made by inserting PCR-amplified fragment with BclI at both ends into the BamHI site in pSG5 vector (Stratagene). To construct mammalian expression plasmids for bovine SF1 and human ERRα1, named pSG5-bSF1 and pSG5-hERRα1, the coding regions for SF1 and ERRα1 were amplified by PCR with an EcoRI site at both ends, and inserted into an EcoRI site of the pSG5 vector. The CAT reporter plasmid, pUMS1.3CAT-(SF1site)$_3$, was prepared by inserting 3 copies of SF1 binding site from human aromatase gene, 5'-CCAAGGTCAGAA-3' (SEQ ID NO:3), into pUMS-64/+5CAT (Zhou and Chen, 1999) through a HindIII site. The transfection of SK-BR-3 cells and CAT assays were carried out as described previously (Wang and Chen, 1992; Zhou and Chen, 1998; Yang et al., 1998).

Figure 4A:
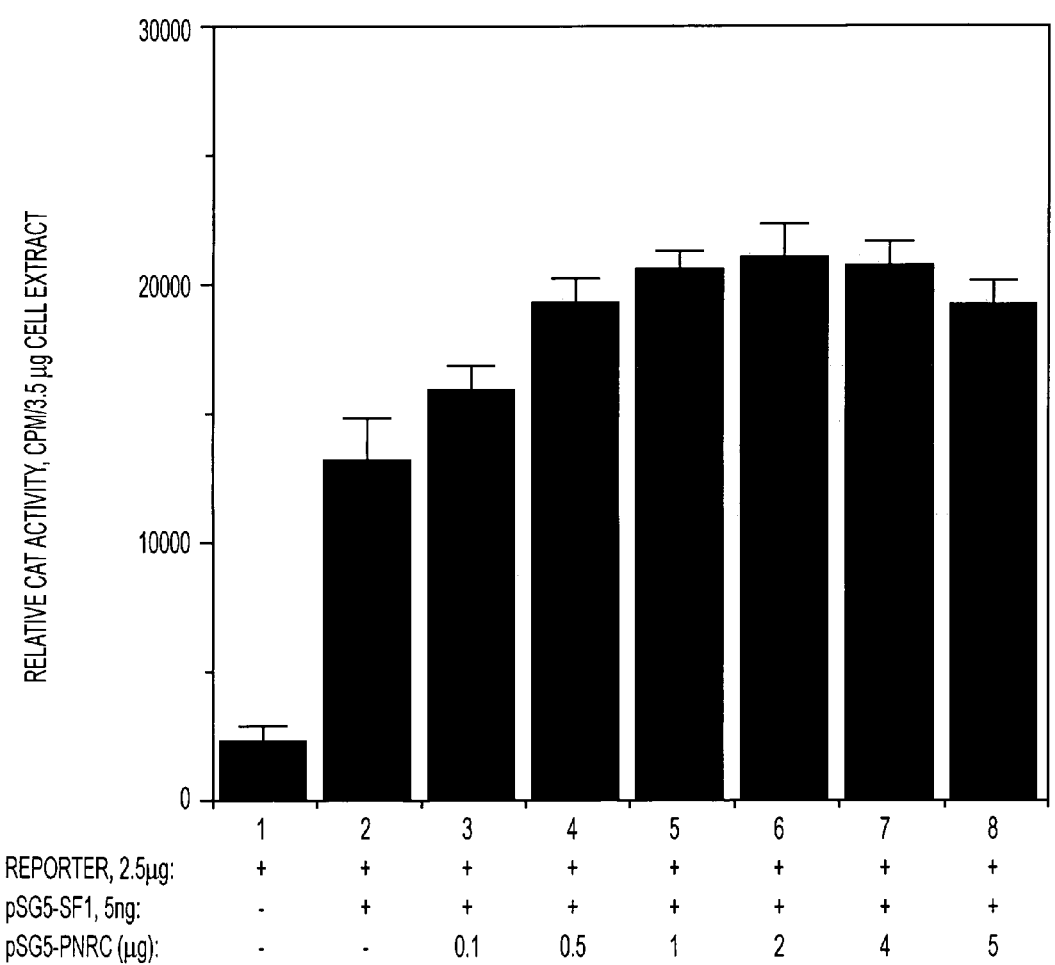
FIGS. 4A-D show the effect of PNRC on nuclear receptor transactivation function.
Figure 4B:
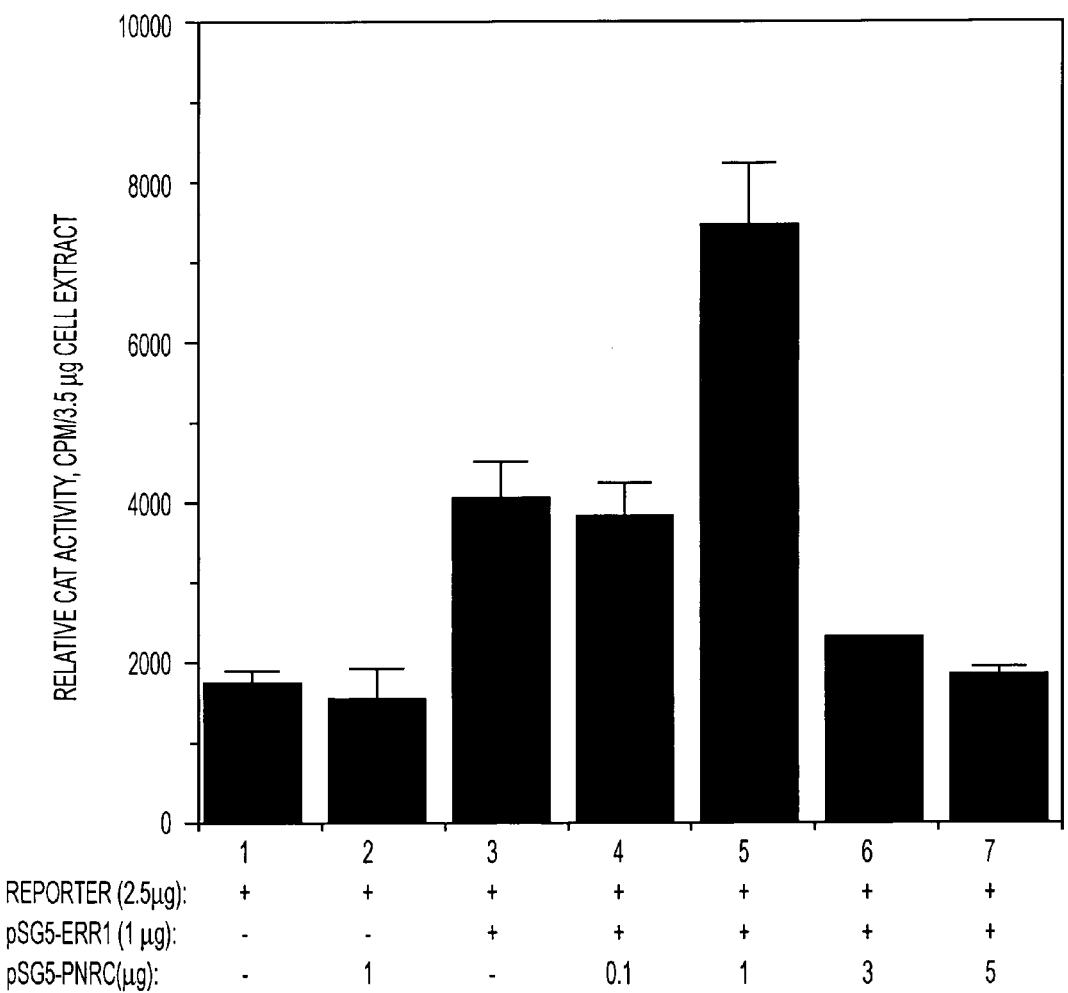
Figure 4C:
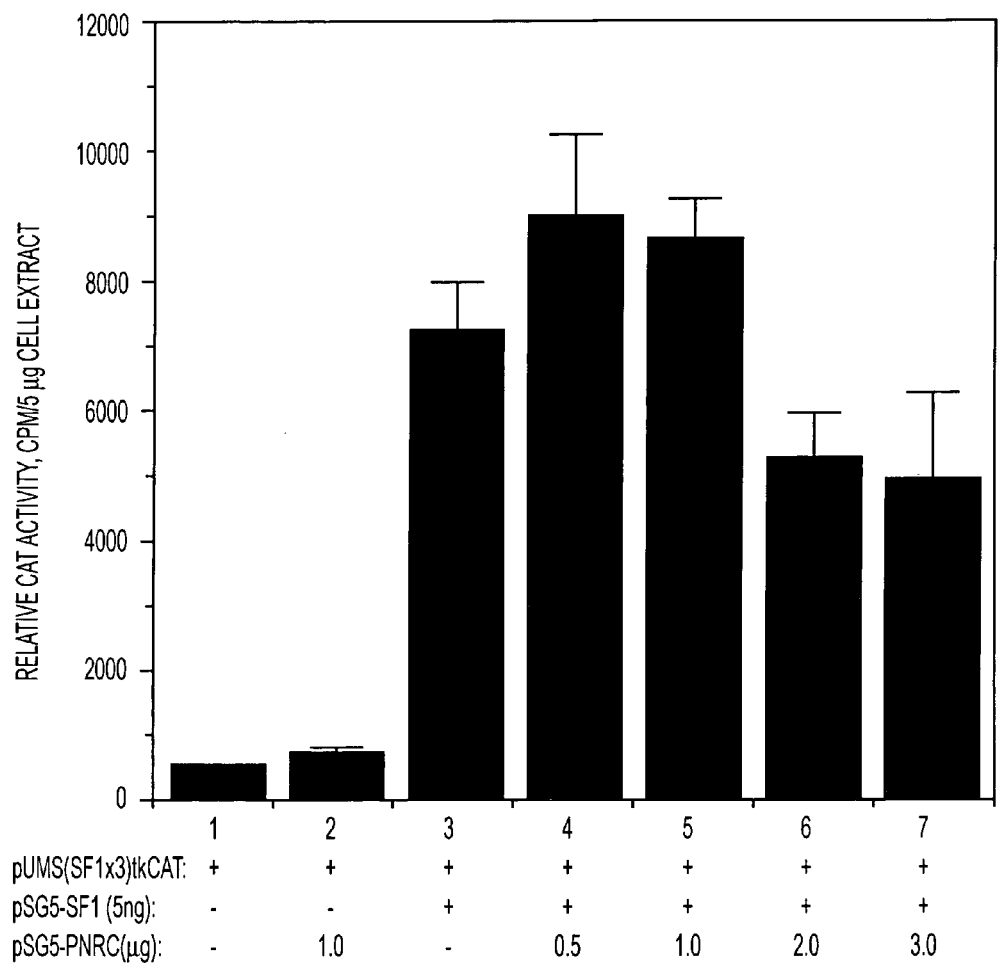
Figure 4D:
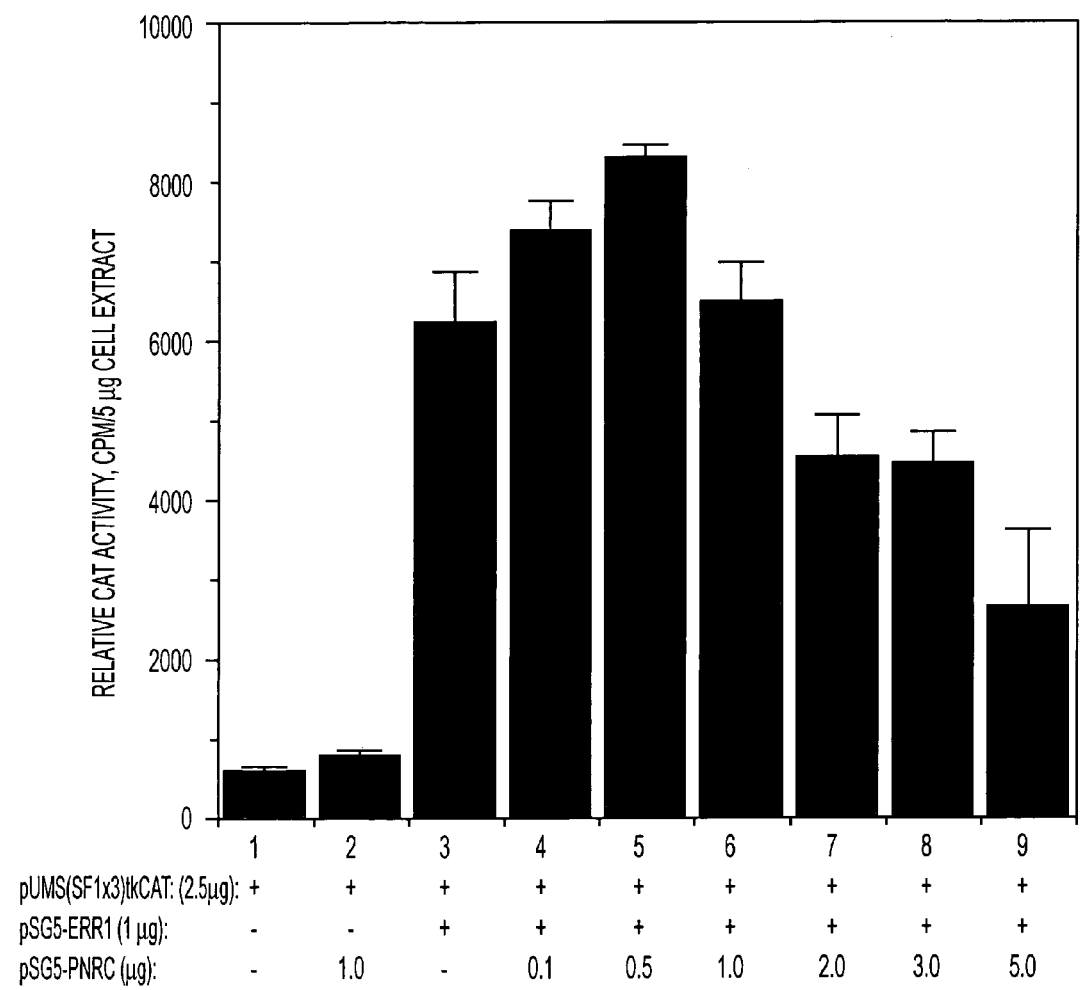

As shown in FIGS. 4A and 4B, both SF1 and ERRα1 can stimulate the transcriptional function of promoter 1.3 of the human aromatase gene. Expression of PNRC in the cells enhanced both SF1-stimulated and ERRα1-stimulated transcription by promoter 1.3 although PNRC has an inhibitory effect on the transactivation activity of both orphan receptors at higher concentrations (FIGS. 4A-B). A similar effect was observed when the promoter in the reporter plasmid was replaced by a thymidine kinase (TK) promoter (FIGS. 4C and 4D). The enhancement of SF1-stimulated transcription by PNRC was moderate and comparable to that by GRIP1 which is a known coactivator. The moderate enhancement of SF1- and ERRα1-stimulated transcription by PNRC may be due to the endogenous levels of PNRC in SK-BR-3 cells.

EXAMPLE 6

Localization of the Interacting Domain within PNRC

Figure 5A:
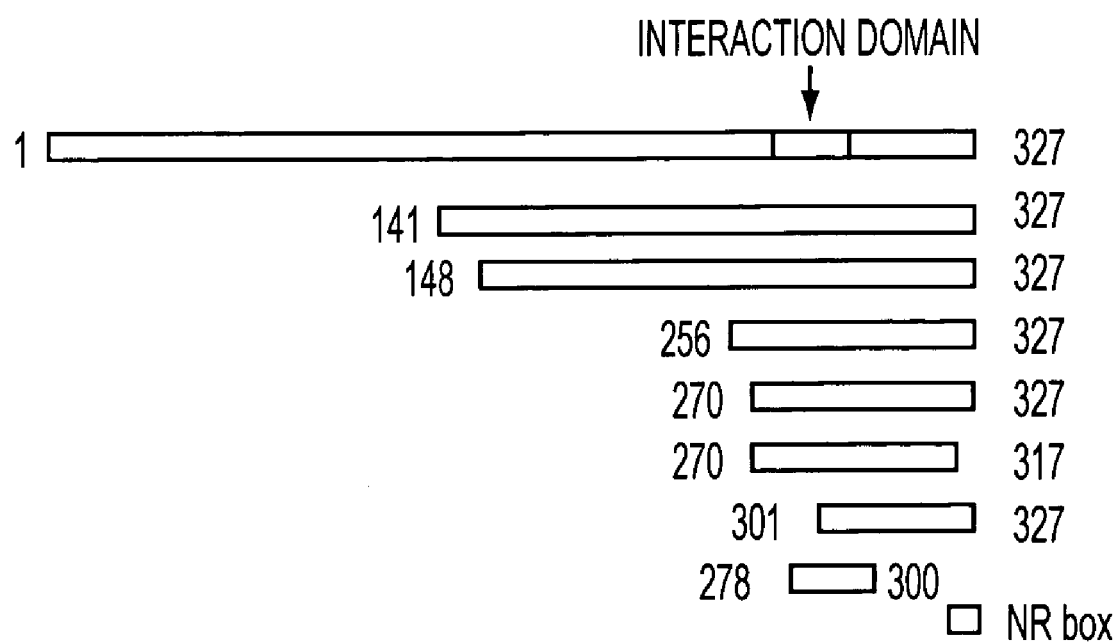
FIG. 5A shows the localization of the interacting domain within PNRC. A series of N-terminal deletion mutants of PNRC were generated and tested for interaction in yeast two-hybrid assays with different nuclear receptors. Gal4AD-PNRC deletion constructs were cotransformed with Gal4DBD-nuclear receptor into yeast strain Y187 and transformants bearing both hybrid plasmids were selected and propagated in the presence of appropriate ligands. The β-galactosidase activities in yeast were determined, expressed in average OD$_{420}$ of three independent assays, the results being shown in FIG. 5B.
Figure 5B:
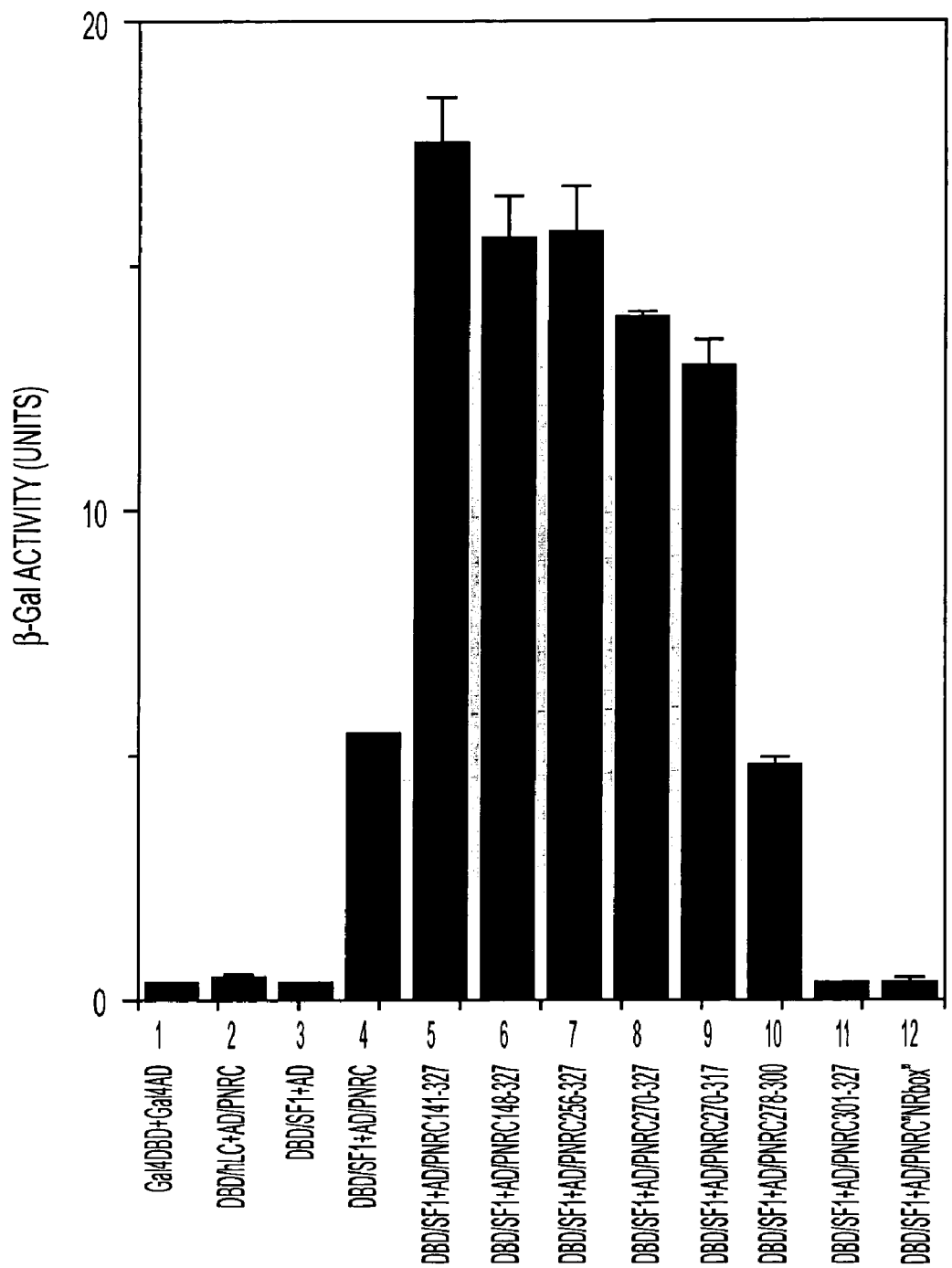

The four PNRC clones originally isolated from the yeast two-hybrid screening encoded four C-terminal peptides, aa 141-327, aa 148-327, aa 256-327 and aa 270-327, respectively. All four clones showed similar binding ability in binding to SF1. Even the shortest peptide, aa 270-327, retained the ability of PNRC to interact with SF1 (FIG. 5B), suggesting that the region containing residues 270 to 327 is responsible for the interaction with SF1. A short conserved peptide motif LXXLL (referred to as the NR box) has been identified and reported to be necessary and sufficient to mediate the binding of several coactivators to liganded nuclear receptors (Heery et al., 1997). There is one NR box-like sequence, LKTLL (aa 319-323; SEQ ID NO:4), in the very end of the C-terminus in PNRC. To examine if this NR box-like sequence is responsible for the interaction, the PNRC fragment coding for aa 270-317 was generated by PCR, expressed as a fusion protein with Gal4 AD, and tested in a yeast two-hybrid assay for its interaction with SF1. Compared to the shortest PNRC clone isolated from library screening, this PNRC fragment has a deletion of the last 10-amino acid segment which contains the NR box. As shown in FIG. 5B, the interaction intensities, as expressed by β-Gal activity, between PNRC/270-327 or PNRC/270-317 and SF1 are about the same, indicating that the NR box sequence in PNRC is not necessary for the interaction. We also expressed this NR box as a fusion protein with Gal4 AD and tested its interaction with SF1 in yeast. No interaction was observed between the NR box and SF1, suggesting again that this NR box sequence is not responsible for the interaction. To directly confirm our findings, yeast expression plasmid for a Gal4AD and PNRC$_{301-327}$ fusion protein (which contains the NR box) was generated and tested in a yeast two-hybrid assay for its interaction with nuclear receptors. As shown in FIG. 5B, this fusion protein could not interact with SF1.

Two additional clones were isolated from the same library screening and found to encode an unknown protein with a regional sequence homology to PNRC. Sequence comparison revealed that there is a 23-amino acid region with 100% identity between PNRC and the novel protein, and this 23 amino acid sequence is within the shortest peptide, i.e., PNRC$_{270-327}$, identified in library screening. This information suggests that the 23-amino acid region, aa 278-300, may be responsible for the interaction. To test if the 23 amino acid region, aa 278-300, is sufficient for interaction, a yeast expression plasmid coding for Gal4AD-PNRC$_{278-300}$ fusion protein was prepared and tested for interaction both in yeast and in mammalian cells. As expected, this 23 amino-acid peptide was found to be able to interact with SF1 (FIG. 5B) and all other nuclear receptors. In addition, PNRC/278-300 was also found to retain most of the interaction of full length PNRC to SF1 in the mammalian two-hybrid assay. Furthermore, the physical interaction between this short 23 residue fragment and SF1 was also demonstrated in the GST pull-down assay (FIGS. 3A-B, lane 4). Together, these results demonstrated that the region from aa278 to aa300 in PNRC is critical and sufficient for interaction with nuclear receptors.

EXAMPLE 7

Mutational Analysis of the Core Ligand Motif for the SH3 Domain in PNRC

Figure 6:
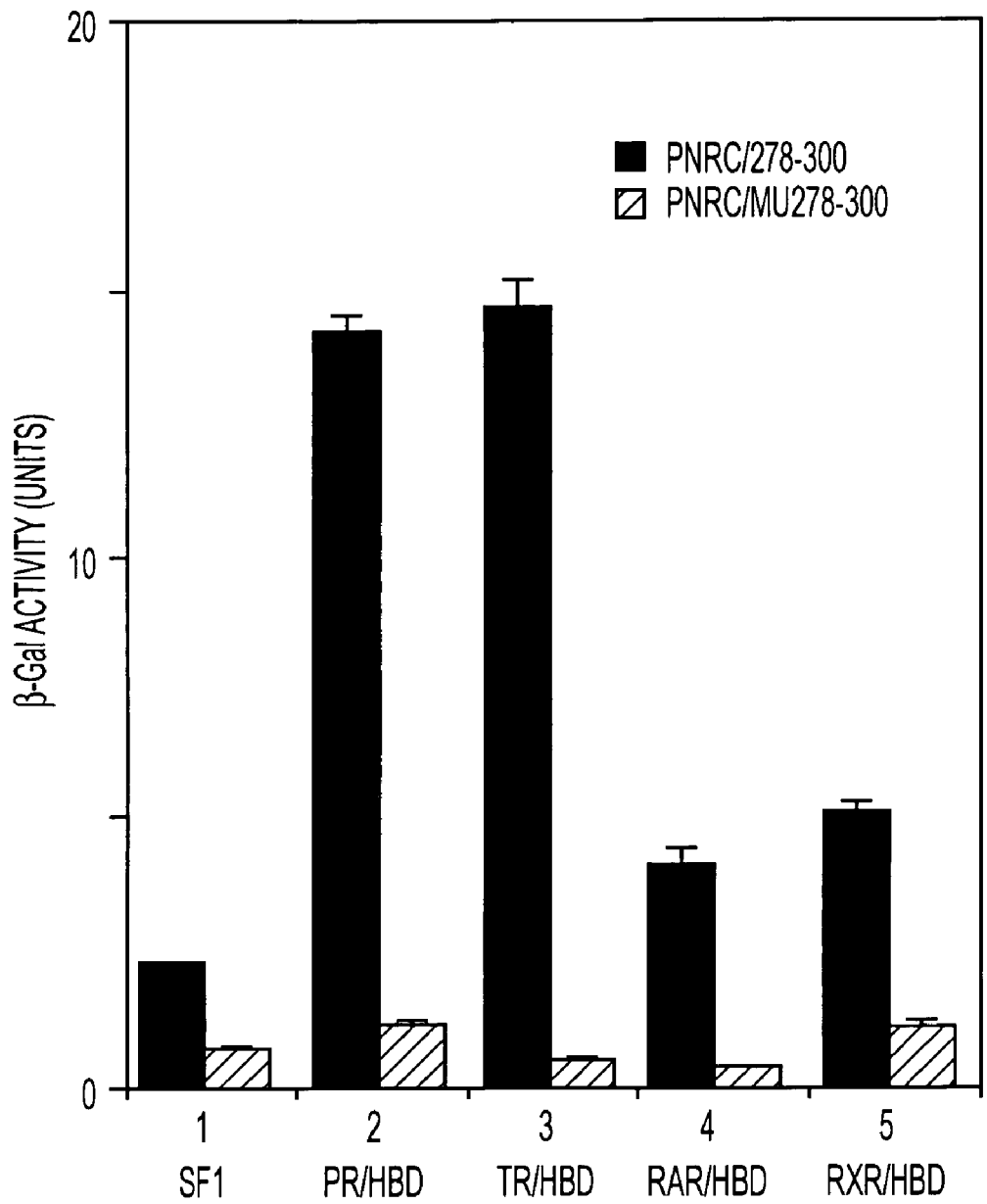
FIG. 6 shows a mutational analysis of the core ligand motif for the SH3 domain in PNRC. The yeast expression plasmid pACT2-PNRC 278-300 (mutant) was prepared as follows: two complementary oligonucleotides with the coding sequences for PNRC278-300 carrying double mutations P287A and P290A were synthesized, annealed, and cloned into pACT2 vector through an EcoRI site. Yeast strain Y187 was cotransformed with pACT2-PNRC$_{278-300\ (wildtype)}$, or pACT2-pNRC$_{278-300\ (mutant)}$, along with each type of the Gal4DBD fusion protein expression plasmids for SF1, PR$_{HBD}$, TR$_{HBD}$, RAR$_{HBD}$, and RXR$_{HBD}$. The Y187 transformants carrying both plasmids were cultured in YPD medium containing a proper ligand (for SF1, no ligand), and the β-galactosidase activity in these cells was determined.

The region from residues 270-327 is rich in proline. Proline-rich sequences have been shown to be targets for binding proteins that contain a Src-homology-3 (SH3) domain (reviewed in Pawson, 1995). Structural and mutagenic analyses of peptide-SH3 complexes (Feng et al., 1994) show that the core ligand for the SH3 domain appears to be a seven-residue peptide containing the consensus X-P-p-X-P, where X tends to be an aliphatic residue and the two conserved prolines (P) are crucial for high affinity binding (Pawson, 1995) ("P" is a crucial proline and "p" is a noncrucial proline). There is a putative core ligand for SH3, S-D-P-P-S-P-S (aa 285-291 (SEQ ID NO:5)), in the aa 278-300 region of PNRC. The biological significance of the core ligand sequence for the SH3 binding domain in PNRC was investigated by the mutagenesis experiments. Double mutations of P287A and P290A in the putative core ligand for SH3, i.e. S-D-P-P-S-P-S (SEQ ID NO:5) to S-D-A-P-S-A-S (SEQ ID NO:6), in the aa 278-300 region of PNRC almost completely abolished the interactions between PNRC278-300 and the nuclear receptors tested including SF1, PR, TR, RAR, and RXR (FIG. 6). This result strongly supports that this SH3-binding motif in the region aa 278-300 is essential for PNRC to interact with the nuclear receptors. However, as shown in FIG. 5B, the interaction between PNRC/270-327 and SF1 is stronger than the interaction between PNRC/278-300 and SF1, suggesting that other residues, especially the aa 270-278 region, may also participate in the interaction with SF1.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

1. Agarwal et al., *J. Clin. Endocrinol. Metab.* 81:3843-3849, 1996.
2. Bingle, *Biochem. Biophys. Res. Commun.* 225:877-882, 1996.
3. Boulikas, *Crit. Rev. Eukaryot. Gene Expr.* 3:193-227, 1993.
4. Cavailles et al., *Proc. Natl. Acad. Sci. USA* 91:10009-10013, 1994.
5. Cavailles et al., *EMBO J.* 14:3741-3751, 1995.
6. Chakravarti et al., *Nature* 383:99-103, 1996.
7. Chen et al., *Biochim. Biophys. Acta* 1264:19-22, 1995.
8. Ding et al., *Mol. Endocrinol.* 12:302-313, 1998.
9. Feng et al., *Science* 266:1241-1247, 1994.
10. Glass et al., *Curr. Opin. Cell Biol.* 9:222-232, 1997.
11. Halachmi et al., *Science* 264:1455-1458, 1994.
12. Hanstein et al., *Proc. Natl. Acad. Sci. USA* 93:11540-11545, 1996.
13. Harada, *J. Steroid Biochem. Mol. Biol.* 61:175-184, 1997.
14. Heery et al., *Nature* 387:733-736, 1997.
15. Hong et al., *Proc. Natl. Acad. Sci. USA* 93:4948-4952, 1996.
16. Horwitz et al., *Mol. Endocrinol.* 10:1167-1177, 1996.
17. Kamei et al., *Cell* 85:403-414, 1996.
18. Le Douarin et al., *EMBO J.* 14:2020-2033, 1995.
19. Lee et al., *Nature* 374:91-94, 1995.
20. Onate et al., *Science* 270:1354-1357, 1995.
21. Pawson, *Nature* 373:573-580, 1995.
22. Shibata et al., *Rec. Progr. Hormone Res.* 52:141-165, 1997.
23. Suzuki, *J. Mol. Biol.* 207:61-84, 1989.
24. Treuter et al., *Mol. Endocrinol.* 12:864-881, 1998.
25. Voegel et al., *EMBO J.* 15:3667-3775, 1996.
26. Vom Baur et al., *EMBO J.* 15:110-124, 1996.
27. Wang and Chen, *Mol. Endocrinol.* 6:1479-1488, 1992.
28. Williamson, *Biochem. J.* 297:249-260, 1994.
29. Yang et al., *Canc. Res.* 58:5695-5700, 1998.
30. Zhou and Chen, *Arch. Biochem. Biophys.* 353:213-220, 1998.
31. Zhou and Chen, *Arch. Biochem. Biophys.* 371:179-190, 1999.
32. Zhou et al., *J. Biol. Chem.* 271:15194-15202, 1996.
33. Zhou et al., *J. Steroid Biochem. Mol. Biol.* 59:163-171, 1996.

The invention claimed is:

1. A method of screening a chemical for its ability to bind to a complex of a proline-rich nuclear receptor co-regulatory protein (PNRC) and a nuclear receptor or nuclear receptor ligand binding domain, wherein said method comprises:
   (a) cotransfecting cells with (i) a nucleic acid encoding a PNRC comprising a peptide selected from the group consisting of SEQ ID NO:8 and SEQ ID NO:9 and (ii) a nucleic acid encoding said nuclear receptor or nuclear receptor ligand binding domain, to produce cotransfected cells which synthesize said PNRC and said nuclear receptor or nuclear receptor ligand binding domain, wherein said cotransfected cells comprise a reporter gene the expression of which depends upon said PNRC binding to said nuclear receptor or nuclear receptor ligand binding domain;
   (b) dividing said cotransfected cells into first and second portions;
   (c) growing said first portion of said cotransfected cells in the presence of said chemical to be screened;
   (d) growing said second portion of said cotransfected cells in the absence of said chemical to be screened; and
   (e) determining the level of expression of said reporter gene in said first and second portions of cells, wherein if the level of expression of said reporter gene in said first portion of cells is greater than the level of expression in said second portion of cells then said chemical binds to said complex of a PNRC and a nuclear receptor or nuclear receptor ligand binding domain.

2. The method of claim 1 wherein said PNRC is SEQ ID NO:9.

3. The method of claim 1 wherein said PNRC is SEQ ID NO:8.

4. The method of claim 1 wherein said nuclear receptor is steroidogenic factor 1 or estrogen related receptor α-1.

5. The method of claim 1 wherein said nuclear receptor ligand binding domain is selected from the group consisting of estrogen receptor, androgen receptor, progesterone receptor, thyroid receptor, retinoic acid receptor and retinoid X receptor.

6. The method of claim 1 wherein said nuclear receptor comprises a binding domain selected from the group consisting of thyroid receptor, progesterone receptor and retinoid X receptor.

7. The method of claim 1 wherein expression of said reporter gene causes production of histidine.

8. The method of claim 1 wherein said reporter gene is the chloramphenicol transferase gene.

9. The method of claim 1 wherein said cells are yeast cells or human cells.

10. The method of claim 1 wherein said nuclear receptor is capable of binding to an aromatase gene.

* * * * *

UNITED STATES PATENT AND TRADEMARK OFFICE
CERTIFICATE OF CORRECTION

PATENT NO. : 7,223,548 B2
APPLICATION NO. : 11/035096
DATED : May 29, 2007
INVENTOR(S) : Chen et al.

It is certified that error appears in the above-identified patent and that said Letters Patent is hereby corrected as shown below:

Title Page; item (56);
    Reference No. 1 on page 1 - Zhou, et al. line 2, "USe" should be -- Use--

Reference No. 8 - Ding, X.F., et al. line 2, "(Grip1)" should be -- (GRIP1) --

Reference No. 9 - Feng, S., et al. line 3, "226" should be -- 266 --

Reference No. 10 - Glass, C.K, et al. line 1, "coativators" should be -- coactivators --

Reference No. 14 - Heery, D.M., et al. line 3, "387" should be -- 387: --

Reference No. 18 - LeDouarin, B., et al. line 3, "teh" should be -- the --

Reference No. 19 - Lee, J.W., et al. line 2, "trasncriptional" should be -- transcriptional --

Reference No. 26, Page 2 - vom Baur, E., et al. line 4, "Jouranl" should be -- Journal--

Reference No. 30 - Zhou, C., et al. line 4, "Mol." should be -- Molec. --

<u>In the Abstract</u>: item (57);

Line 11, "BAR" should be -- RAR --

UNITED STATES PATENT AND TRADEMARK OFFICE
CERTIFICATE OF CORRECTION

PATENT NO. : 7,223,548 B2
APPLICATION NO. : 11/035096
DATED : May 29, 2007
INVENTOR(S) : Chen et al.

It is certified that error appears in the above-identified patent and that said Letters Patent is hereby corrected as shown below:

In the Specification:

Col. 5, line 41, "pNRC" should be -- PNRC --

Col. 11, line 1, insert --, -- between "ER" and "AR"

Signed and Sealed this

Eighteenth Day of December, 2007

JON W. DUDAS
*Director of the United States Patent and Trademark Office*